United States Patent
Piest et al.

(10) Patent No.: US 12,214,027 B2
(45) Date of Patent: Feb. 4, 2025

(54) STABILISATION OF LIVE MOLLICUTES BACTERIA IN A LIQUID COMPOSITION

(71) Applicant: Intervet inc., Rahway, NJ (US)

(72) Inventors: Martin Piest, Afferden (NL); Edwin Kets, Heilig Landstichting (NL); Paul Vermeij, St. Anthonis (NL); Marian Anna Catharina Jozefina Heijnen, Arcen (NL); Nöel Dautzenberg, Nijmegen (NL)

(73) Assignee: INTERVET INC., Rahway, NJ (US)

( * ) Notice: Subject to any disclaimer, the term of this patent is extended or adjusted under 35 U.S.C. 154(b) by 614 days.

(21) Appl. No.: 17/441,768

(22) PCT Filed: Mar. 27, 2020

(86) PCT No.: PCT/EP2020/058649
§ 371 (c)(1),
(2) Date: Sep. 22, 2021

(87) PCT Pub. No.: WO2020/201048
PCT Pub. Date: Oct. 8, 2020

(65) Prior Publication Data
US 2022/0175902 A1 Jun. 9, 2022

(30) Foreign Application Priority Data
Mar. 29, 2019 (EP) .................................... 19166362

(51) Int. Cl.
A61K 39/02 (2006.01)
A61K 39/00 (2006.01)

(52) U.S. Cl.
CPC ...... *A61K 39/0241* (2013.01); *A61K 2039/52* (2013.01); *A61K 2039/552* (2013.01)

(58) Field of Classification Search
None
See application file for complete search history.

(56) References Cited

U.S. PATENT DOCUMENTS

| 4,226,940 A | 10/1980 | Storrs |
| 2014/0271710 A1 | 9/2014 | Buchanan et al. |
| 2015/0246114 A1 | 9/2015 | Qiao et al. |

FOREIGN PATENT DOCUMENTS

| CN | 105992593 A | 10/2016 |
| CN | 105992593 B | 3/2020 |
| JP | 2014520807 A | 8/2014 |
| JP | 2017505807 A | 2/2017 |
| WO | WO 2010037514 A2 | 4/2010 |
| WO | WO 2010037514 A3 | 4/2010 |
| WO | WO 2013006842 A2 | 1/2013 |
| WO | WO 2013006842 A3 | 1/2013 |
| WO | 2015121463 A2 | 8/2015 |
| WO | 2016108083 A1 | 7/2016 |
| WO | 2017222377 A1 | 12/2017 |
| WO | WO 2018211454 A2 | 11/2018 |
| WO | WO 2018211454 A3 | 11/2018 |

OTHER PUBLICATIONS

Faggian, Marta, Natural Deep Eutectic Solvents (NADES) as a Tool for Bioavailability Improvement: Pharmacokinetics of Rutin Dissolved in Proline/Glycine after Oral Administration in Rats: Possible Application in Nutraceuticals, Molecules, 2016, 1531 (pp. 1-11), vol. 21, No. 11.
Gupta, R.S., et al., Phylogenetic framework for the phylum Tenericutes based on genome sequence data: proposal for the creation of a new order Mycoplasmoidales ord. nov., containing . . . , Antonie van Leeuwenhoek, 2018, pp. 1583-1630, 111.
Gutiérrez, M.C., et al., Bacteria Incorporation in Deep-eutectic Solvents through Freeze-Drying, Wiley Interscience, Angew. Chem. Int. Ed., 2010, pp. 2158-2162, 49.
Paiva, Alexandre, Natural Deep Eutectic Solvents—Solvents for the 21st Century, ACS Sustainable Chemistry & Engineering, 2014, 1063-1071, 2(5).
Qiao, Y. et al., Effects of natural deep eutectic solvents on lactic acid bacteria viability during cryopreservation, Applied Microbiology and Biotechnology, 2018, pp. 1-11, https://doi.org/10.1007/s00253-018-8996-3.
Dai et al., 2015, "Tailoring properties of natural deep eutectic solvents with water to facilitate their applications," Food Chem., 187:14-19.
Li et al., 2018, "Protective Effect of Natural Deep Eutectic Solvent on Green Fluorescent Protein," Modern Food Science and Technology, 34(10):44-48, in Chinese with English abstract.
Meng et al., 2015, "Research Progress in Isolation and Identification Methods of Mycoplasma in Animals," Shanghai Animal Husbandry and Veterinary Newsletter, 2:27-29, in Chinese with machine English translation.
Qin et al., 2002, "Current Status and Problems of Molecular Classification in the Phytoplasmas," Scientia Silvae Sinicae, 38(6):125-136, in Chinese with English abstract.
Radosevic et al., 2018, "Antimicrobial, cytotoxic and antioxidative evaluation of natural deep eutectic solvents," Environ. Sci. Pollut. Res. Int., 25(14):14188-14196.

*Primary Examiner* — Jennifer E Graser
(74) *Attorney, Agent, or Firm* — JONES DAY

(57) ABSTRACT

The present invention relates to a liquid composition of live Mollicutes bacteria and a stabiliser, whereby the stabiliser is a natural deep-eutectic solvent (NADES). In this liquid composition the live Mollicutes are stabilised without need for freezing or freeze-drying. This allows various advantageous uses in diagnostics and medicine, specifically as a liquid vaccine for use against infection or disease caused by Mollicutes bacteria, for human- or non-human animals.

14 Claims, 6 Drawing Sheets

Figure 2

A

Mycoplasma synoviae stored at RT

Figure 1:
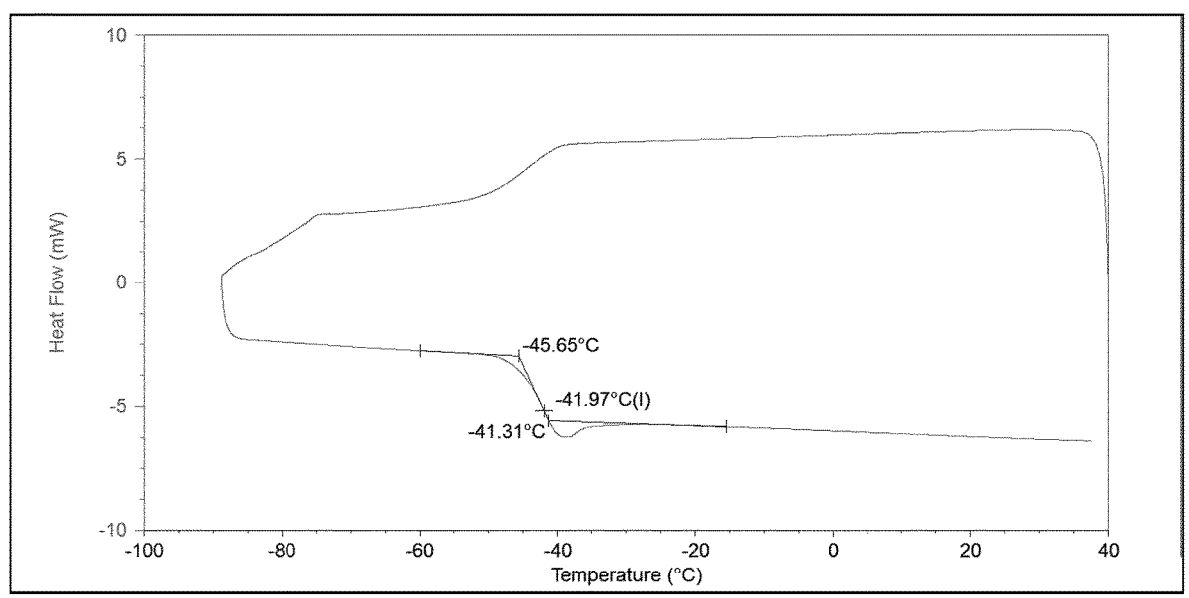

(Bar chart; Survival (Log10 CFU/ml) vs formulation)

- PRO:SOR:WFI 1:1:2.5 — t=0: 6.5
- BET:SOR:WFI 1:1:2.5 — t=0: 7.9; t=2 wk: 6.2; t=5 wk: 3.7
- CHOL:XYL:WFI 2:1:2.5 — t=0: 7.2
- ARG:SOR:WFI 1:2:6 — t=0: 8.0; t=2 wk: 7.0
- SOR:XYL:TRE:WFI 2:2:1:10 — t=0: 7.3; t=2 wk: 5.9; t=5 wk: 4.9
- PBS — 9.0

Legend: ■ t = 0  ▨ t = 2 wk  ▢ t = 5 wk  ▧ t = 8 wk

B

Mycoplasma synoviae stored at 2-8 °C

(Bar chart; Survival (Log10 CFU/ml) vs formulation)

- PRO:SOR:WFI 1:1:2.5 — t=0: 7.6; t=12 wk: 7.1
- BET:SOR:WFI 1:1:2.5 — t=0: 8.2; t=12 wk: 7.8
- CHOL:XYL:WFI 2:1:2.5 — t=0: 8.0; t=12 wk: 6.5
- ARG:SOR:WFI 1:2:6 — t=0: 7.3; t=12 wk: 5.1
- SOR:XYL:TRE:WFI 2:2:1:10 — t=0: 7.9; t=12 wk: 6.9
- PBS — 9.0

Legend: ■ t = 0  ▢ t = 12 wk  ▤ t = 24 wk

Figure 3
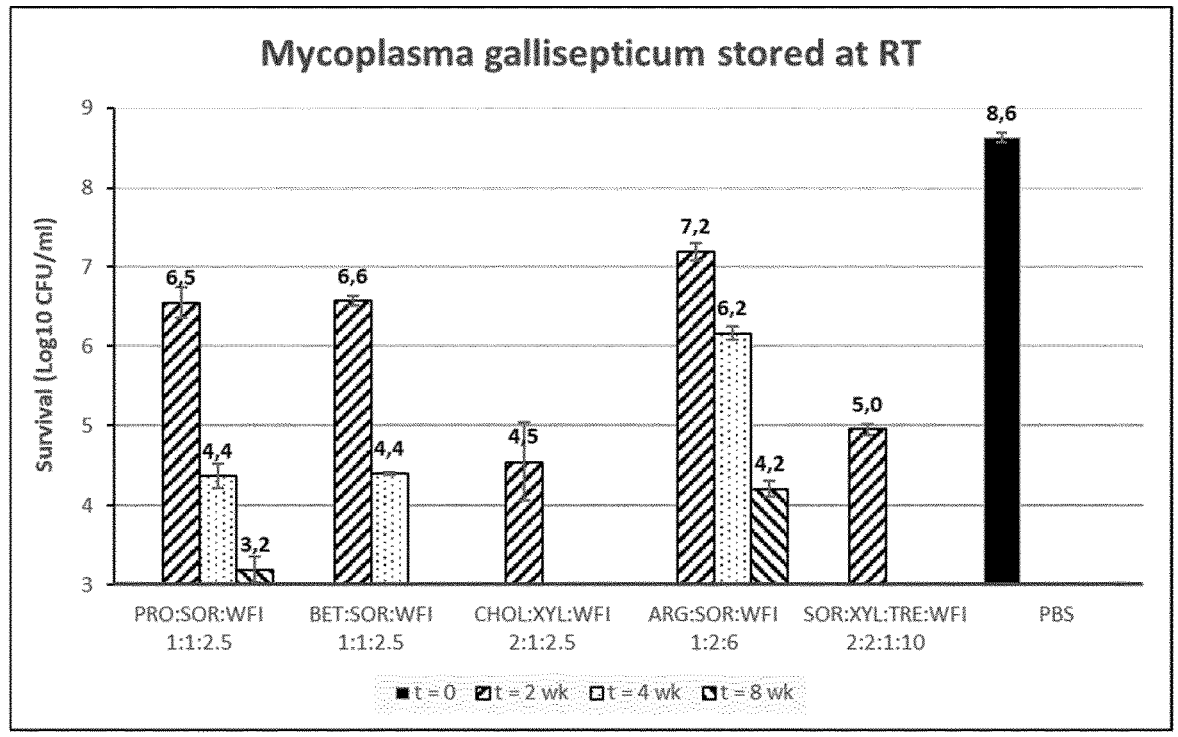
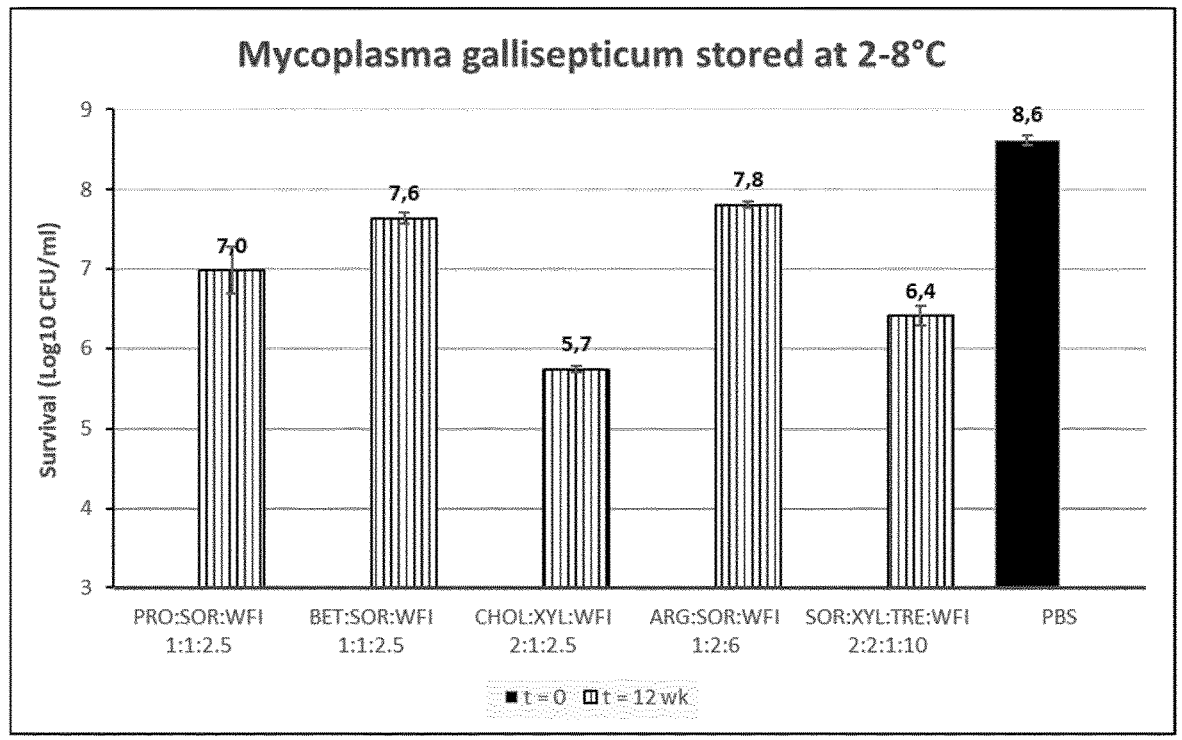

Figure 5
A
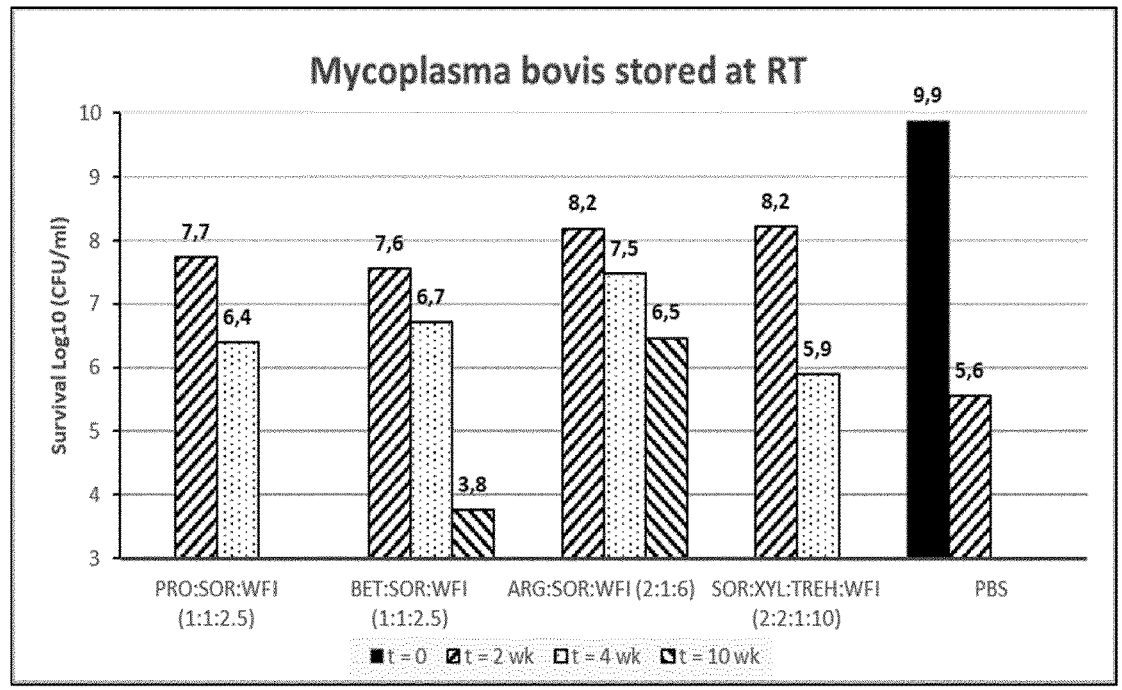
B
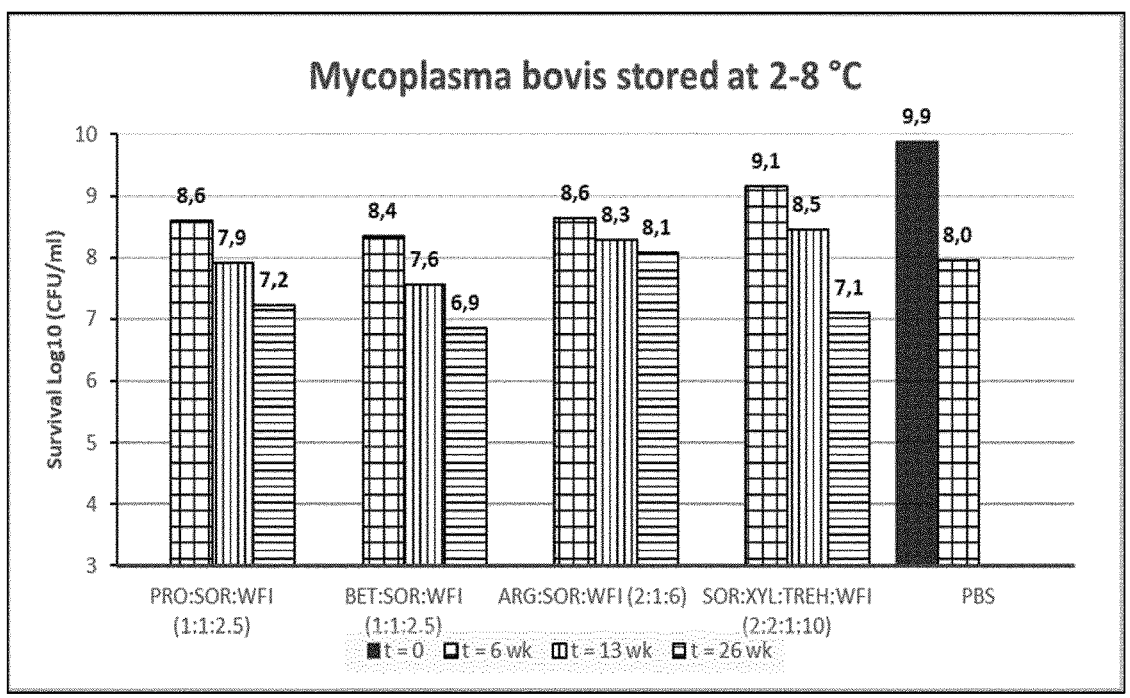

Figure 6
A
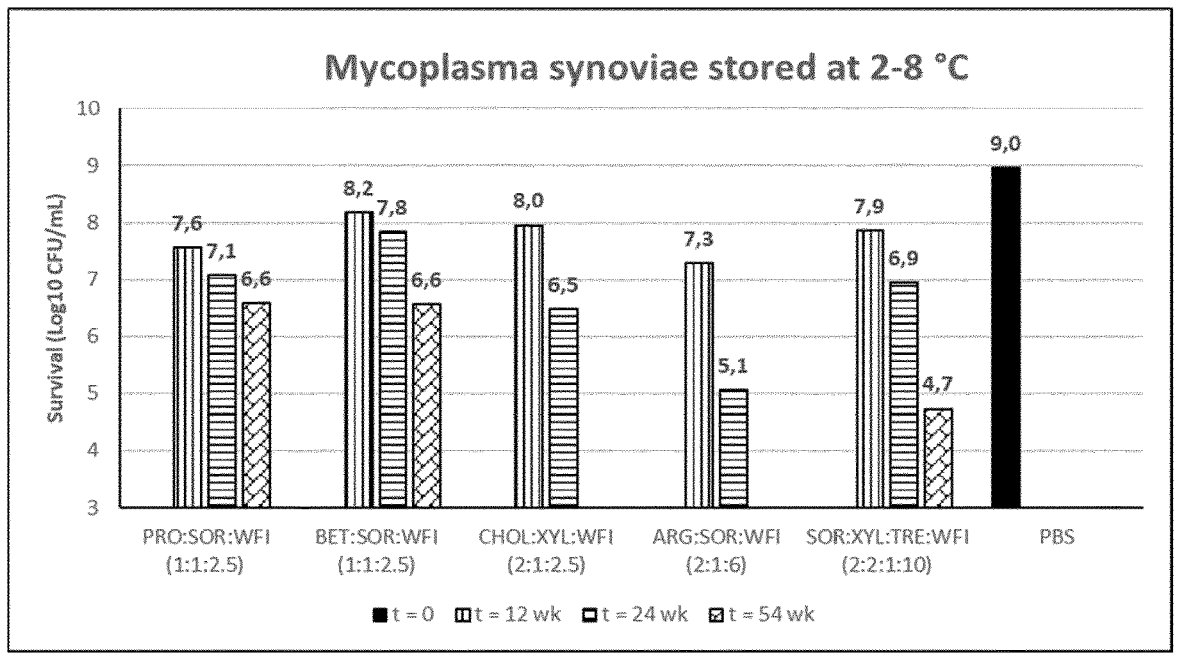
B
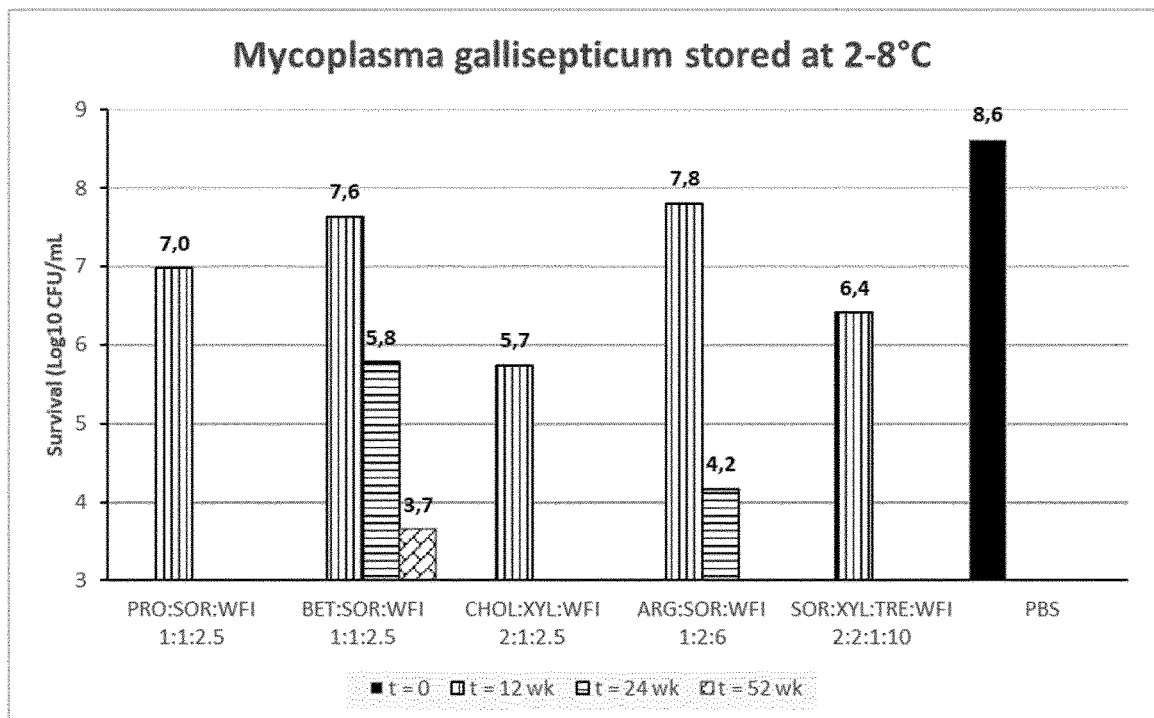

STABILISATION OF LIVE MOLLICUTES BACTERIA IN A LIQUID COMPOSITION

CROSS-REFERENCE TO RELATED APPLICATIONS

This application is a National Stage application of International Patent Application No. PCT/EP2020/058649, filed Mar. 27, 2020, which claims priority to European Patent Application No. 19166362.4, filed Mar. 29, 2019.

The present invention relates to the fields of bacteriology and vaccinology. Specifically, the invention regards a liquid composition of live Mollicutes bacteria and a stabiliser, the manufacture of said liquid composition, the use of a NADES as a stabiliser in said composition, and various medical uses of said composition.

Live bacteria are being used in a wide variety of applications, well known are classical- or modern biotechnological processes, diagnostics and vaccines. Important for all those applications are ways to stabilise such bacteria during storage and use, to maintain their viability. Common techniques rely on storage in deep-frozen condition, using cryoprotectants such as glycerol or rich media for stabilisation. Alternatively, the live bacteria can be lyophilised, and kept in freeze-dried form at refrigerated or frozen conditions. However, all these methods of stabilisation have a number of disadvantages: the rich storage media introduce components of undefined- and variable quality, such as sera, hydrolysates, and extracts. Such an undefined ingredient may have an unpredictable effect on stability. Further the frozen products require a laborious cold-chain for storage and delivery. But even these processes do not provide full survival of live bacterial cells, as the freezing steps themselves induce significant loss of viable cell-count. Also, lyophilisation is a very costly and time-consuming process. Therefore, improved ways to effectively stabilise the live cell count of bacteria during storage and use, are highly desirable.

A group of bacteria with agricultural and medical significance is the class Mollicutes. These are classified taxonomically in the phylum of the Tenericutes (Ludwig et al., 2009, in: Bergey's Manual of Systematic Bacteriology, 2nd edn, vol. 3. Springer: New York, USA, pp 1-13.). This phylum contains bacteria that derive from Gram positive bacteria but have lost their cell wall. They are typically parasites or commensals of eukaryotic hosts.

Infections of animals by *Mycoplasma* bacteria, either as primary- or as secondary pathogen, often cause respiratory disease and/or a variety of other symptoms which together can cause mild to severe disease, causing much discomfort to the affected host, as well as economic damage. A reference for the effects of *Mycoplasma* infections in agriculture is: "The Merck veterinary manual" (11th ed., 2016, ISBN-10: 9780911910612).

While infection with *Mycoplasma* bacteria can be treated therapeutically with certain types of antibiotics, commonly vaccines are being used prophylactically. Such vaccines can be based on live attenuated strains, or on inactivated bacterins (killed bacteria). A bacterin vaccine against *M. bovis* is MpB Guard™ (Agrilabs). Most used commercial *Mycoplasma* vaccines are for poultry; examples are: live attenuated vaccines for *M. gallisepticum*: Vaxsafe® MG (Bioproperties) (frozen), and Nobilis MG 6/85 (MSD Animal Health) (freeze-dried, cooled); and bacterin vaccines for *M. gallisepticum*: MG-Bac® (Zoetis) and Nobilis® MG inac (MSD Animal Health), both emulsions with an oil adjuvant. Live attenuated vaccines for *M. synoviae* are: Vaxsafe® MS (Bioproperties) (frozen), and Nobilis® MS Live (MSD Animal Health) (freeze-dried, cooled). Several other live attenuated *Mycoplasma* vaccines are known and are being used on a more limited scale, e.g. Contavax™, a freeze-dried vaccine against the ruminant *M. mycoides*, which is used in some African countries. Also, in China a live attenuated *M. hyopneumoniae* vaccine is used for swine. Reviews of *Mycoplasma* vaccination are: Whithear (1996, Rev. Sci. Tech. Off. Int. Epiz., vol. 15, p. 1527-1553); Kleven (2008, Av. Dis., vol. 52, p. 367-374); and Perez-Casal et al. (2017, Vaccine, vol. 35, p. 2902-2907).

Because of their association with the cell-membrane or even their invasion of host cells, Mollicutes are well-known contaminants of in vitro cell-cultures of a variety of eukaryotic cells. Therefore, several species of live Mollicutes bacteria are used for diagnostic- and quality control purposes. This is also a formal requirement in biological production, under governmental regulations such as the European Pharmacopoeia and the American 9 CFR.

The Mollicutes are the smallest self-replicating organisms known: bacteria from some species are only 0.2 micrometre in diameter, and some have a genome of only 580 kbp. Having so few genes, makes that Mollicutes bacteria heavily rely on resources from their environment, so when cultured in vitro they typically require very rich media. Also, the lack of a cell wall exposes their cell-membrane to physical and chemical environmental influences, resulting in poor stability upon storage and during use.

An important problem in the vaccine industry is therefore how to preserve the viability of such live Mollicutes bacteria as bacterial stocks, during the shelf-life of the finished product, and during use in e.g. diagnostics or vaccination. One solution is to produce and use non-live, bacterin type vaccines. However, such vaccines are relatively expensive because of their requirement for a relative high dose, repeated administration, and the use of an adjuvant.

Vaccines based on live Mollicutes bacteria are stored deep-frozen or freeze-dried, and in rich stabilising media. As described, such media are less desirable for a number of reasons. Also, significant losses in viable cell counts still occur from the freezing process itself, causing a loss of up to $10^3$ colony forming units (CFU) within days. Consequently, methods and materials for improving the stabilisation of live Mollicutes bacteria are therefore highly desirable.

Deep eutectic solvents (DES) are well-known liquid compositions that combine a number of remarkable properties. In general, these are mixtures of compounds that are liquid at ambient temperatures but have a low water content. Also, the small amount of water that is present is tightly bound, limiting its availability for chemical or biological processes. This is represented by very low water activity values. DES are for example described by Abbott et al., 2003, Chem. Commun., vol. 1, p. 70-71, and in WO 2009/120839.

Being highly ionic, but at the same time very low in water activity, DES are very effective as solvents for polar hydrophobic compounds. Examples range from the extraction of gasses, minerals, or industrial bulk products, to the solubilisation of pharmaceuticals. DES have also been used for the extraction and stabilisation of biomolecules such as enzymes and RNA, see U.S. Pat. No. 8,247,198 and WO 2011/155829, respectively.

Since about 2011 a special form of DES is being considered, composed of naturally occurring substances. These so-called 'natural DES', or NADES, are described e.g. in: Choi et al., 2011, Plant Physiol., vol. 156, p. 1701-1705; and Dai et al. 2013, Anal. Chim. Acta, vol. 766, p. 61-68.

NADES currently receive much interest as 'green' solvents, which can be used for the extraction of natural products, and as solvents for use e.g. in natural pesticides.

WO 2011/155829 describes the extraction of biological materials using NADES. One of the options listed is the extraction of proteinic materials such as subunit-vaccines.

Similarly, WO 2014/131906 describes amongst others, a fixative for a virus in blood or tissue, with special focus on the extraction and stabilisation of the viral RNA for clinical diagnostics. The fixative is a DES, and while WO 2014/131906 lists a large number of possible DES compositions, actual use is made only of compositions comprising urea or trifluoroacetamide as the proton-acceptor, and choline or betaine as the proton donor. In WO 2014/131906 the most preferred DES is composed of choline-chloride and trifluoroacetamide, which is therefore not a NADES, and trifluoroacetamide is not an acceptable pharmaceutical excipient.

WO 2016/108083 describes the use of NADES for their bactericidal activity: several NADES were found to be able to effectively kill or inactivate Gram-positive and Gram-negative bacteria, as well as fungal cells of *Candida*.

WO 2016/162703 describes the use of NADES made e.g. of betaine and an organic acid or a polyol, for the extraction of biological molecules, specifically from plant materials.

WO 2017/222377 describes the use of a NADES gel in a mixture with animal feed, to provide a source of water that does not dry out under heat. The specific use described is for newly hatched chicks.

WO 2015/121463 describes liquid stable poultry vaccines, specifically of poultry viruses, in a composition of 5-40% sugar alcohol, and 0.15-0.75 M of an amino acid selected from arginine, glutamic acid or glycine. Most importantly however, WO 2015/121463 and similar publications such as WO 2014/029702, and WO 2014/140239, do not disclose a NADES, but describe aqueous solutions that contain at least 60% w/v of water, and have a water activity ($a_w$) above 0.85. In the Examples section comparative data are provided.

Gutierrez et al. (2010, Angew. Chem. Int. Ed., vol. 49, p. 2158-2162) describe the cryopreservation of the Gram-negative bacterium *Escherichia coli* using a NADES-dilution made of Choline Chloride and Glycerol in 1:2 molar ratio, with 20% w/v of solute. To form the NADES, the mixture of bacteria and NADES-dilution was freeze-dried.

Qiao et al. (2018, Appl. Microbiol. Biotechnol., vol. 102, p. 5695-5705) tested the stabilisation of lactic acid bacteria using compositions derived from NADES. These bacteria are Gram-positive and contain a cell-wall. The viability of two species from the genus *Lactobacillus* was not stabilised or was even damaged by the use of NADES in frozen storage. *Streptococcus thermophilus* could be stabilised in frozen form using a NADES of Proline:Glycerol in 1:3 molar ration. However, by applying a 1+1 volume mix of NADES and bacterial culture, Qiao et al. diluted their NADES to a point where the network of hydrogen-bonds is no longer intact. This is evident from the differential scanning calorimetry (DSC) profile (Qiao et al., FIG. 4) showing melting and growth of ice crystals. These are the properties of an aqueous composition, whereas an intact NADES would show a glass-transition temperature.

Qiao et al. also describe that having a cell-wall makes bacteria resistant to the effects of NADES toxicity, namely: dehydration and cell membrane damage.

It is an object of the present invention to overcome a disadvantage in the prior art, and to accommodate to a need in the field by providing a composition comprising live Mollicutes bacteria that can be prepared without freeze-drying and does not need to be kept frozen, but provides sufficient stabilisation during storage and handling at temperatures above 0° C.

Surprisingly it was found that this object can be met, and consequently one or more disadvantages of the prior art can be overcome, by providing a liquid composition that is able to stabilise live Mollicutes bacteria without freezing or freeze-drying. This is achieved by employing a NADES as a stabiliser.

This discovery opens up a number of very favourable applications: live Mollicutes bacteria can now be stored without freezing or freeze-drying, which processes themselves harm the viability. Also, such processes are laborious, time consuming and expensive. Further, the liquid composition of the present invention does not employ components of undefined or variable quality, such as hydrolysates for stabilisation, but on the contrary uses compounds that are of natural origin and chemically defined. In addition, being in liquid form allows ease of use in various applications such as diagnostics, quality control, but also in the use as live attenuated vaccines. This because the NADES are acceptable as pharmaceutical carrier. Such vaccinations can now be administered using the liquid composition comprising live Mollicutes bacteria, either directly or after dilution.

It was unexpected that a NADES would be able to stabilise live Mollicutes bacteria: as powerful ionic solvents, NADES were expected to dissolve the delicate and exposed bacterial cell-membrane and extract their cytoplasmic proteins and nucleic acids. In fact, Qiao et al. (supra) warn that bacteria without cell-wall are sensitive to the toxicity of NADES. Also, WO 2016/108083 (supra) actually employs NADES for killing bacteria.

The inventors were therefore surprised to find that NADES formulations were able to provide significant stabilisation of the viability of live Mollicutes bacteria, without freezing or freeze-drying. The stabilisation was significantly better than that observed for aqueous liquid compositions. For example, *M. synoviae* could be kept in a liquid composition according to the invention at 4° C. for up to 24 weeks, with a loss of less than 3 Log 10 CFU, and in some compositions the loss was even less than 1 Log 10 CFU. Even at room temperature significant stabilisation was found for up to 8 weeks, showing a loss of only 4 Log 10 CFU, while the culture in phosphate buffered saline was completely lost within one week at that temperature.

It is not known exactly how or why a NADES is such an effective stabiliser for live Mollicutes bacteria. Although the inventors do not want to be bound by any theory or model that might explain these findings, they speculate that the low amount of available water in a NADES is helpful in maintaining bacterial viability. Also, Mollicutes bacteria apparently interact with NADES in a way that is different from the way for bacteria that have a cell-wall. Because there is no prior art on the stabilisation of Mollicutes bacteria in NADES this effect could not have been predicted.

Therefore, in one aspect the invention provides a liquid composition comprising live Mollicutes bacteria and a stabiliser, characterised in that the stabiliser is a natural deep-eutectic solvent (NADES).

The term "liquid" is used in its common meaning, referring to a composition that can flow at a certain temperature and in a certain time period. One way to determine liquid properties is a tilt test wherein a container with a composition at a certain temperature is tilted, and when after a certain amount of time any change of form of the composition is detected, that composition is classified as being a liquid. For the invention a composition is liquid if it changes shape within 15 minutes of its container being tilted by 90°, at room temperature.

The term "comprising" (as well as variations such as "comprise", "comprises", and "comprised") as used herein, intends to refer to all elements, and in any possible combination conceivable for the invention, that are covered by or included in the text section, paragraph, claim, etc., in which this term is used, even if such elements or combinations are not explicitly recited; and not to the exclusion of any of such element(s) or combinations.

Thus, any such text section, paragraph, claim, etc., can therefore also relate to one or more embodiment(s) wherein the term "comprising" (or its variants) is replaced by terms such as "consist of", "consisting of", or "consist essentially of".

The term "live" is used here in its common meaning in respect of bacteria, referring to their ability to grow, move, take up and ferment nutrients, and/or replicate under appropriate conditions. Methods to determine if bacteria are dead or alive are well-known in the art. This can be determined in vivo, but more conveniently in vitro, for example by culturing in a suitable medium and detecting increase in the culture's optical density, or by plating on suitable agar plates and counting of CFUs. Alternative is to apply a live/dead selective staining and counting.

The term "Mollicutes" refers to bacteria having the characterising features of their taxonomic class, such as the morphologic, genomic, and biochemical characteristics, as well as the biological characteristics such as physiologic, immunologic, or pathologic behaviour. The same applies for a reference to a bacterial order, family, genus, or to names of individual bacterial species.

The Mollicutes class contains the orders of the Acholeplasmatales, the Anaeroplasmatales, the Entomoplasmatales, and the Mycoplasmatales. The Acholeplasmatales order contains the well-known Mollicutes plant-pests of the (*Candidatus*) *Phytoplasma* genus. The Entomoplasmatales order contains insect commensals and plant pathogens of the genus *Spiroplasma*.

Most well-known is the Mycoplasmatales order, as it contains well known human- or animal pathogenic bacteria of the genus *Mycoplasma*: e.g. *M. pneumoniae*, *M. bovis*, *M. hyopneumoniae*, *M. meleagridis* and *M. gallisepticum*, which (mainly) infect respectively: humans, ruminants, swine, turkeys, and chickens.

As is known in the field, the classification of a microorganism in a particular taxonomic group is based on a combination of such features. The invention therefore also includes species of Mollicutes bacteria from the orders, families, genera, and species that are classified under the Mollicutes class. Similarly, this refers to bacteria that are sub-classified therefrom in any way, for instance as a subspecies, strain, isolate, genotype, variant, subtype or subgroup, and the like.

Further, it will be apparent to a person skilled in the field of the invention that while a particular order, family, genus or species of Mollicutes bacteria for the invention may currently be assigned to that group, however that is a taxonomic classification that could change in time as new insights can lead to reclassification into a new or different taxonomic group. However, as this does not change the bacterium itself, or its antigenic repertoire, but only it's scientific name or classification, such re-classified bacteria remain within the scope of the invention. For example, Gupta et al. (2018, Antonie van Leeuwenhoek, vol. 111, p. 1583-1630) have proposed a new framework for the phylum Tenericutes, based on the latest genome data.

Samples of Mollicutes bacteria for use in the invention can be obtained from a variety of sources, e.g. as field isolate from a human, or from a non-human animal in the wild or on a farm, or from various laboratories, (depository) institutions, or (veterinary) universities.

A "stabiliser" for the invention is a composition capable of reducing a loss in the number of viable cells of the Mollicutes bacteria for the invention, resulting from handling or use, and/or from storage at a certain temperature over a certain period of time.

The 'stabilisation' for the invention is expressed as the effect on the difference in CFU before and after a certain treatment of a composition comprising live Mollicutes bacteria, e.g. from an incubation for a certain period of time at a certain temperature. The survival in different liquid compositions according to the invention is thereby compared to that in a standard PBS buffer (10 mM $Na_2PO_4$, 1.8 mM $KH_2PO_4$, 2.7 mM KCl and 137 mM NaCl, in water at pH 7.4). Any survival above that observed in PBS under similar storage conditions is then considered a survival effect provided by the liquid composition according to the invention.

A "deep-eutectic solvent" (DES) is well-known in the art as an ionic liquid comprising a mixture of at least two compounds at a molar ratio that forms a eutectic mixture, whereby the eutectic point of the mixture is significantly lower than the melting points of the individual compounds.

This reduced melting point of the mixture is caused by the interaction of the compounds, one acting as hydrogen-bond donor, and one other acting as hydrogen-bond acceptor, which provides a network of stable hydrogen-bonds. While the network does incorporate a small amount of water, this cannot crystallise upon freezing. This allows the mixture to be in liquid form at temperatures considerably below the melting points of the constituents. Commonly 'eutectic' means: easy melting.

A NADES for use in the invention has an intact hydrogen-bond network. This can conveniently be verified by thermal analysis of its phase-transition profile using DSC. Consequently, a NADES for use in the invention has a DSC profile that shows a glass-transition temperature.

The determination of a DSC profile is well known and can be done using standard equipment. An example profile is presented in FIG. 1.

The hydrogen-bond network can allow a limited level of dilution. However, when too much dilution is applied, the DES' will turn into a regular aqueous solution. In that case the DSC profile will display a melt- and a crystallisation enthalpy, as in Qiao et al., supra, FIG. 4.

The individual compounds (excluding the water) used for forming the NADES for the invention have melting points above about 80° C., and the resulting NADES has a melting point below about 40° C. For example: the melting points of betaine and sorbitol are 310° C. and 95° C. respectively, while a NADES formed at a molar ratio for betaine, sorbitol, and water of 1:1:2.5, has a glass transition temperature of −50° C. and did not show ice crystallisation and/or an ice melting point in its DSC profile.

The term "natural" serves to indicate that the compounds used to form the natural DES (NADES) for the invention, are organic compounds that under normal conditions can be found in material from biological sources such as plants or animals, in amounts well above trace amounts. Typically, such a natural compound is, or is derived from, a primary metabolite that is present in a specific material of vegetable or animal origin. As the skilled person will appreciate, the term natural is only used herein to characterise the initial origin of a compound for use in a NADES for the invention, and not to characterise the actual source of the compound to be used for the invention. Thus, the natural compound may also be used for the invention when derived via (semi-) synthetic production.

Examples of natural compounds that can be used to form a NADES for the invention, are organic acids, amines, sugars, sugar alcohols, amino acids, and quaternary ammonium salts such as choline-derivatives.

It will be evident to the person skilled in the art of the field of the invention, that within the embodiments disclosed herein for the invention there will be combinations of a certain type of NADES and a type of Mollicutes bacterium that are more favourable than other combinations, with regard to the bacterium's stability. Nevertheless, the skilled person will be readily capable of selecting, optimizing, and fine-tuning combinations and composition according to the present invention, using nothing but routine methods and materials, with the information as disclosed herein.

Further details of preferred embodiments and of further aspects of the invention will be described below.

The water that is present in a NADES for use in the invention is tightly bound in the NADES hydrogen-bond network structure, which strongly reduces the water's availability for chemical or biological processes that could influence the stability of the Mollicutes bacteria. This feature is commonly expressed by indicating the amounts of total water and of free water. The availability of that water (the free water) is indicated by the value of the water activity, indicated by the symbol: $a_w$. The water activity varies between the upper limit of 1.0 for pure water, and the lower limit of 0. Water activity is commonly measured by comparing (at the same temperature) the vapour pressure of a test composition, relative to that of pure water and to a number of saturated salt-solutions of known water activity. This is described in different handbooks, reviews, and manuals, such as for example on the conservation of fruits and vegetables in the FAO agricultural service bulletin no. 149 (Cánovas et al, FAO, Rome, 2003, ISBN 92-5-104861-4); and a review is: 'Fundamentals of water activity', Decagon Devices Inc., Washington, 2015 (http://pdf.directindustry.com/pdf/decagon-devices-inc/fundamentals-water-activity/64142-634433.html).

At a water activity below about 0.8 growth of most bacteria is stopped; below 0.7 growth of most yeasts and moulds is stopped; and at a water activity below 0.4 most enzyme activity is effectively stopped.

Equipment and procedures to measure water activity are well-known and available, for instance by using headspace pressure analysis.

It was found that effective stabilisation of Mollicutes bacteria in liquid compositions according to the invention can be achieved when the composition has a water activity below about 0.85.

Therefore, in an embodiment of the liquid composition according to the invention, the composition has a water activity of 0.85 or less.

For the invention, the indicated water activity refers to the water activity of the liquid composition according to the invention in the form of a final product, for example such as is offered by a commercial producer, and in which form it can be stored for prolonged time. Upon use of this composition it may be diluted or mixed with other components, which may then change the water activity value.

In an embodiment of the liquid composition according to the invention, the water activity of the composition is less than about 0.8; more preferably less than about 0.7, about 0.6, about 0.5, about 0.4, about 0.3, or even less than about 0.2, in this order of preference.

Preferably the water activity of the liquid composition according to the invention is between 0.8 and 0.1. More preferably between 0.7 and 0.1, 0.6 and 0.1, 0.5 and 0.1, 0.4 and 0.1, 0.3 and 0.1, or even between 0.2 and 0.1, in this order of preference.

For the invention the indication of a range intends to include the stated end-points.

For the invention "about" indicates that a number can vary between ±10% around its indicated value. Preferably "about" means ±9% around its value, more preferably "about" means ±8, 7, 6, 5, 4, 3, 2, 1 or even 0% around its value, in that order of preference.

The water used for the liquid composition according to the invention is preferably water of high quality and purity, such as (multiply) distilled water or reverse osmosis water. More preferably the water is of pharmaceutical quality grade and suitable for parenteral injection; such quality of water is typically sterile, and essentially free from pyrogens, for example: water for injection (WFI).

The NADES for use in the liquid composition according to the invention is prepared with a limited amount of water. By varying the water content of the liquid composition, its properties can be adapted and optimised, for example regarding the viscosity of the liquid composition. Effective NADES-containing compositions with little viscosity can be created with a total water content up to 50% w/w (Dai et al., 2015, vol. 187, p. 14-19). Higher amounts of water may disturb the network of hydrogen bonds of the NADES.

Therefore, in an embodiment of the liquid composition according to the invention, the composition has a water content of 50% w/w or less.

The water content of the liquid composition according to the invention, is expressed as a percentage of weight per weight "w/w", which is the weight of the total amount of water in the liquid composition according to the invention, as part of the weight of the liquid composition. Water content can be measured using different procedures, for example by Karl Fischer titration, well-known in the art.

As for the water activity, the liquid composition in this context is the composition in the form of a final product, before any mixing or diluting is applied.

Preferably the liquid composition according to the invention has a water content of 40% w/w or less, more preferably of 30, 25, 20, 15, 10, 8, 7, 6, or even of 5% w/w or less, in that order of preference.

The lower limit of the water content in the liquid composition according to the invention will be determined by practical factors, such as: how little water suffices for the solubilisation of the compounds that form the NADES. Also: how much water is required to reach an acceptable level of viscosity of the NADES so that it can conveniently be processed or used.

Therefore, in an embodiment of the liquid composition according to the invention, the water content in the liquid composition is between 50 and 0.5% w/w; between 40 and 1% w/w; between 30 and 1.5% w/w; between 20 and 2% w/w; or even between 10 and 3% w/w, in this order of preference.

Further, an amount of water is introduced into the mixture by the admixing of the NADES with a sample of live Mollicutes bacteria, to prepare the liquid composition according to the invention. However, the liquid composition of the invention should not be overly diluted.

Therefore, in an embodiment of the liquid composition according to the invention, the ratio of the volumes of the NADES to that of the bacterial sample to be combined, will preferably be at least 3:1 v/v of NADES:bacterial sample; more preferably at least 5:1 v/v NADES:bacterial sample; or even at least 10:1 v/v NADES:bacterial sample, in this order of preference. NB: a ratio of 10:1 means the combination of 9 parts of NADES with 1 part of bacterial sample. For example: a NADES of proline, sorbitol, and water at a molar ratio of 1:1:2.5 has a total amount of water of 13.1% w/w. After admixing with a sample of Mycoplasma bacteria for the invention, at a ratio of 9 parts NADES+1 part bacteria, the total amount of water of the resulting liquid composition according to the invention, is 21.8% w/w.

To limit overly diluting the NADES for the invention into an aqueous composition, the bacterial sample to be combined may need to be concentrated.

It was found that NADES effective as stabiliser for live Mollicutes bacteria, in a liquid composition according to the invention, were formed from different combinations and ratios of an organic salt and/or a polyol, or were formed from several polyols.

Therefore, in an embodiment of the liquid composition according to the invention, the NADES comprises an organic salt and a polyol.

In an alternate embodiment of the liquid composition according to the invention, the NADES comprises two or more compounds that are all polyols.

In some of these embodiments the network of hydrogen-bonds is formed by the organic salt as the ionic species which acts as the hydrogen bond donor, and the polyol as the hydrogen bond acceptor. Alternatively, when the NADES comprises only polyols, the network is formed by hydrogen-bonds between these molecules.

For the invention, a "polyol" is an organic compound containing two or more hydroxyl groups. However, very large polymers that are under the definition of a polyol, such as cellulose, are not very effective at forming a NADES as defined herein, thus should preferably not be used in the invention. Consequently, polyols for use in the invention preferably have a molecular weight of less than about 10.000 grams per Mole.

In a further preferred embodiment, the polyols for use in the invention have a molecular weight of less than 5000, or even less than 1000 grams per Mole.

The compounds for use in the NADES for use in the invention are readily available in different purities and qualities from a variety of commercial suppliers. Preferably the compounds are used in a pharmaceutical grade quality. Such excipients are for example described in governmental regulations such as the European Pharmacopoeia and the American 9 CFR, and in handbooks such as: The Handbook of Pharmaceutical Excipients (R. Rowe et al., Pharmaceutical press 2012, ISBN 0857110276); Remington: the science and practice of pharmacy (2000, Lippincot, USA, ISBN: 683306472), and: "Veterinary vaccinology" (P. Pastoret et al. ed., 1997, Elsevier, Amsterdam, ISBN 0444819681).

Preferred polyols for use in the invention are sugars or sugar-alcohols, as these have demonstrated to be versatile components that allow the generation of a variety of effective NADES for use in the invention.

In a preferred embodiment the sugar is a non-reducing sugar.

In an embodiment of the non-reducing sugar for use in the liquid composition according to the invention, the non-reducing sugar is selected from sucrose and trehalose.

Preferably the non-reducing sugar is trehalose. Trehalose is preferably CAS nr. 6138-23-4.

For the invention "sugar alcohols" are hydrogenated sugars, that comprise 3 or more carbon atoms, and can be based on mono-, di-, or poly-saccharides.

In an embodiment of the sugar-alcohol for use in the liquid composition according to the invention, the sugar-alcohol is one or more selected from: erythritol, xylitol, and sorbitol.

Erythritol is preferably CAS nr. 149-32-6. Xylitol is preferably CAS nr. 87-99-0. Sorbitol is preferably D-sorbitol, CAS nr. 50-70-4.

In an embodiment of the sugar-alcohol for use in the liquid composition according to the invention, the sugar-alcohol is one or more selected from: xylitol and sorbitol.

In a more preferred embodiment the sugar alcohol is sorbitol.

The polyol for use in the liquid composition according to the invention can be used as different salts, isomeric forms, hydrate- or anhydrous forms, etcetera. The skilled person is perfectly capable of selecting and testing a suitable form of the polyol for use in the invention.

For the invention, the "organic salt" is a salt of any organic acid or base, including zwitterions, that is within the definition of being a natural compound as presented herein above, and that is capable of forming a deep-eutectic solvent for the invention as described herein. A skilled person is perfectly capable of selecting an organic salt for the present invention and applying that to form a NADES.

In an embodiment of the liquid composition according to the invention, the organic salt is one or more selected from salts of: betaine, proline, choline, methionine, and arginine.

For the invention, 'betaine' is preferably the compound N,N,N-trimethylglycine, CAS nr. 107-43-7, which is also known as glycine-betaine. Proline is preferably CAS nr. 609-36-9. Choline is preferably CAS nr. 62-49-7. Methionine is preferably L-methionine, CAS nr. 63-68-3.

In a preferred embodiment the choline is choline-chloride, CAS nr. 67-48-1.

As for the polyol described above, the organic salt can be used in different isomeric forms, hydrate- or anhydrous forms, etcetera. The skilled person is perfectly capable of selecting and testing a suitable form of an organic salt for use in the invention.

In an embodiment of the liquid composition according to the invention, when the organic salt is argine, the arginine is used as a mixture of L-arginine (CAS nr. 74-79-3) and L-arginine-HCl (CAS nr 1119-34-2), whereby the L-arginine-HCl is the majority the mixture.

Such a mixture of arginine compounds helps to bring the pH value of the liquid composition according to the invention closer to physiological values, when the composition is diluted, e.g. before use as a vaccine, or when plating out for counting.

Preferably the molar ratio of L-arginine to L-arginine-HCl is between 1:1 and 1:100; more preferably the molar ratio of L-arginine to L-arginine-hydrochloride is between 1:1 and 1:50, more preferably the molar ratio is about 1:19.

In an embodiment of the liquid composition according to the invention, the NADES comprises three polyols.

In a preferred embodiment the three polyols are sorbitol, xylitol, and trehalose.

In an embodiment of the NADES for use in the liquid composition according to the invention, the organic salt is selected from salts of: betaine, proline, choline and arginine; and the polyol is selected from: xylitol, and sorbitol.

For the invention, the organic salt and the polyol, or the polyols, can be applied in different molar ratios to each other, to provide NADES with different properties. These can be optimised by a skilled person to arrive at an optimal stabilisation of live Mollicutes bacteria in the liquid composition according to the invention.

Therefore, in an embodiment of the liquid composition according to the invention, the molar ratio between the organic salt and the polyol, all as defined herein, is between 1:5 and 5:1.

In a preferred embodiment of the liquid composition according to the invention, the molar ratio between the organic salt and the polyol, all as defined herein, is between 1:4 and 4:1, between 1:3 and 3:1, or even is between 1:2 and 2:1, in this order of preference.

In an embodiment of the liquid composition according to the invention, the molar ratio between any of the three polyols xylitol, trehalose, and sorbitol, all as defined herein, can be between 1 and 5 fold. Consequently, the molar ratio of sorbitol:xylitol:trehalose, is between 1:1:1 and one of: 1:1:5, 1:5:1, 5:1:1, 1:5:5, 5:1:5, 5:5:1, and 5:5:5.

One type of advantageous use of the liquid composition according to the invention, is for use as a vaccine. In such application, the Mollicutes bacteria are used as the active ingredient of a live bacterial vaccine, which requires them to be of attenuated character, so as not to cause unacceptable vaccination-reaction in the target animal.

Therefore, in an embodiment of the liquid composition according to the invention, the Mollicutes bacteria are attenuated in respect of their pathogenic properties.

The term "attenuated" for the invention is used in its common meaning, referring to a bacterium that causes a lower level of pathogenic effects from having a reduced rate of infection and/or of replication in the host, as compared to the unmodified, non-attenuated, or 'wildtype' form of such a Mollicutes bacterium. Such attenuated live bacterium is also called a 'modified live' bacterium.

Attenuation of a Mollicutes bacterium can be obtained in different ways, for example by passaging of a wild type bacterium through experimental animals or in cell-culture, by use of mutagens, or via recombinant DNA technology, all well known in the art.

The liquid composition according to the invention is effective at stabilising the viability of a variety of bacteria from the Mollicutes class.

Therefore, in an embodiment the Mollicutes bacteria are one or more selected from the bacterial order: Acholeplasmatales, Anaeroplasmatales, Entomoplasmatales, and Mycoplasmatales.

In an embodiment the Mollicutes bacteria for the invention are one or more selected from the bacterial family of: Acholeplasmataceae, Anaeroplasmataceae, Entomoplasmataceae, Spiroplasmataceae, and Mycoplasmataceae.

In an embodiment the Mollicutes bacteria for the invention are one or more selected from the bacterial genus of: *Acholeplasma, Phytoplasma, Anaeroplasma, Asteroleplasma, Entomoplasma, Mesoplasma, Spiroplasma, Hepatoplasma, Marinoplasma, Moeniiplasma, Mycoplasma*, and *Ureaplasma*.

Preferably the Mollicutes bacteria for the invention are one or more selected from the bacterial genus of: *Acholeplasma, Spiroplasma* and *Mycoplasma*.

More preferably the Mollicutes bacteria for the invention are from the bacterial genus *Mycoplasma*.

In an embodiment of the liquid composition according to the invention, the Mollicutes bacteria are one or more selected from *M. pneumoniae, M. bovis, M. hyopneumoniae, M. meleagridis, M. gallisepticum*, and *M. synoviae*.

In a preferred embodiment, the Mollicutes bacteria are *M. gallisepticum* and/or *M. synoviae*.

In an embodiment of the liquid composition according to the invention, the Mollicutes bacteria are *M. gallisepticum* and *M. synoviae*.

Experiments showed that *M. gallisepticum* and *M. synoviae* could be stored in combination in a liquid composition according to the invention, whereby no significant effect from one on the stability of the other could be detected, when tested up to 23 weeks at 2-8° C. In such mixtures, the two species of bacteria could be detected and counted when plating out the same mix-sample on two different types of agar plates: one type of plate containing NAD (nicotinamide adenine dinucleotide) and one type without NAD, and comparing colony numbers counted. As described in literature (Olson & Kish Meadows, 1972, Avian Dis., vol. 16, p. 387-396), *M. synoviae* requires NAD for its growth, therefore on the plates without NAD, all colonies observed are from *M. gallisepticum*.

In a preferred embodiment, the liquid composition according to the invention is capable of providing a stabilisation of the live Mollicutes bacteria, whereby the number of CFU of the Mollicutes is not reduced by more than 3 Log 10 after incubation at 4° C. for 12 weeks. Even more preferred, the number of CFU of the Mollicutes is not reduced by more than 7 Log 10 after incubation at room temperature for 8 weeks.

Room temperature is a temperature of 20±5° C.; 4° C. is 2 to 8° C.

In an embodiment of the liquid composition according to the invention, one, or more, or all of the conditions apply, selected from the group consisting of:
- the liquid composition has a water activity of 0.85 or less;
- the water activity of the liquid composition is less than about 0.8; more preferably less than about 0.7, about 0.6, about 0.5, about 0.4, about 0.3, or even less than about 0.2, in this order of preference;
- the water activity of the liquid composition is between 0.8 and 0.1; more preferably between 0.7 and 0.1, 0.6 and 0.1, 0.5 and 0.1, 0.4 and 0.1, 0.3 and 0.1, or even between 0.2 and 0.1, in this order of preference;
- the liquid composition has a water content of 50% w/w or less;
- the liquid composition has a water content of 40% w/w or less, more preferably of 30, 25, 20, 15, 10, 8, 7, 6, or even of 5% w/w or less, in that order of preference;
- the water content in the liquid composition is between 50 and 0.5% w/w; between 40 and 1% w/w; between 30 and 1.5% w/w; between 20 and 2% w/w; or even between 10 and 3% w/w, in this order of preference;
- the ratio of the volumes of the NADES to that of the bacterial sample to be combined, will preferably be at least 3:1 v/v of NADES:bacterial sample; more preferably at least 5:1 v/v NADES:bacterial sample; or even at least 10:1 v/v NADES:bacterial sample, in this order of preference;
- the NADES comprises an organic salt and a polyol;
- the NADES comprises two or more compounds that are all polyols;
- the polyols for use in the invention have a molecular weight of less than 5000, or even less than 1000 grams per Mole;
- the polyol is a sugar or a sugar-alcohol;
- the sugar is a non-reducing sugar;

the non-reducing sugar is selected from sucrose and trehalose; preferably the non-reducing sugar is trehalose; trehalose is preferably CAS nr. 6138-23-4;

the sugar-alcohol is one or more selected from: erythritol, xylitol, and sorbitol;

erythritol is preferably CAS nr. 149-32-6; xylitol is preferably CAS nr. 87-99-0; sorbitol is preferably D-sorbitol, CAS nr. 50-70-4;

the sugar-alcohol is one or more selected from the group of: xylitol and sorbitol; in a more preferred embodiment the sugar alcohol is sorbitol;

the organic salt is one or more selected from salts of: betaine, proline, choline, methionine, and arginine;

betaine is preferably the compound N,N,N-trimethylglycine, CAS nr. 107-43-7, which is also known as glycine-betaine; proline is preferably CAS nr. 609-36-9; choline is preferably CAS nr. 62-49-7; methionine is preferably L-methionine, CAS nr. 63-68-3; arginine is preferably L-arginine, CAS nr. 74-79-3;

the choline is choline-chloride, CAS nr. 67-48-1;

when the organic salt is argine, the arginine is used as a mixture of L-arginine (CAS nr. 74-79-3) and L-arginine-hydrochloride (CAS nr 1119-34-2);

the molar ratio of L-arginine to L-arginine-HCl is between 1:1 and 1:100; more preferably the molar ratio of L-arginine to L-arginine-hydrochloride is between 1:1 and 1:50, more preferably the molar ratio is about 1:19;

the organic salt is selected from salts of: betaine, proline, choline, and arginine; and the polyol is selected from: xylitol, and sorbitol;

the molar ratio between the organic salt and the polyol, is between 1:5 and 5:1;

the molar ratio between the organic salt and the polyol, is between 1:4 and 4:1, between 1:3 and 3:1, or even is between 1:2 and 2:1, in this order of preference;

the NADES comprises three polyols; in a preferred embodiment the three polyols are sorbitol, xylitol, and trehalose;

the molar ratio of sorbitol:xylitol:trehalose, is between 1:1:1 and one of: 1:1:5, 1:5:1, 5:1:1, 1:5:5, 5:1:5, 5:5:1, and 5:5:5;

the Mollicutes bacteria are attenuated in respect of their pathogenic properties;

the Mollicutes bacteria are one or more selected from the bacterial order: Acholeplasmatales, Anaeroplasmatales, Entomoplasmatales, and Mycoplasmatales;

the Mollicutes bacteria are one or more selected from the bacterial family of: Acholeplasmataceae, Anaeroplasmataceae, Entomoplasmataceae, Spiroplasmataceae, and Mycoplasmataceae;

the Mollicutes bacteria are one or more selected from the bacterial genus of: *Acholeplasma, Phytoplasma, Anaeroplasma, Asteroleplasma, Entomoplasma, Mesoplasma, Spiroplasma, Hepatoplasma, Marinoplasma, Moeniiplasma, Mycoplasma*, and *Ureaplasma;* the Mollicutes bacteria are one or more selected from the bacterial genus of: *Acholeplasma, Spiroplasma* and *Mycoplasma;* the Mollicutes bacteria are from the bacterial genus *Mycoplasma;* the Mollicutes bacteria are one or more selected from *M. pneumoniae, M. bovis, M. hyopneumoniae, M. meleagridis, M. gallisepticum*, and *M. synoviae;* the Mollicutes bacteria are *M. gallisepticum* and/or *M. synoviae;* and the Mollicutes bacteria are *M. gallisepticum* and *M. synoviae.*

In an embodiment of the liquid composition according to the invention, the liquid composition has a water activity of 0.85 or less, and a water content of 50% w/w or less; the NADES comprises an organic salt and a polyol, wherein the polyol is xylitol or sorbitol, and the organic salt is selected from betaine, proline, choline, and arginine; the Mollicutes bacteria are attenuated in respect of their pathogenic properties, and the Mollicutes bacteria are one or more selected from *M. pneumoniae, M. bovis, M. hyopneumoniae, M. meleagridis, M. gallisepticum*, and *M. synoviae.*

In a preferred embodiment, the Mollicutes bacteria are *M. gallisepticum* and/or *M. synoviae*, and the NADES comprises betaine and sorbitol.

In an embodiment of the liquid composition according to the invention, the liquid composition has a water activity of 0.85 or less, and a water content of 50% w/w or less; the NADES comprises three polyols which are sorbitol, xylitol, and trehalose; the Mollicutes bacteria are attenuated in respect of their pathogenic properties, and the Mollicutes bacteria are one or more selected from *M. pneumoniae, M. bovis, M. hyopneumoniae, M. meleagridis, M. gallisepticum*, and *M. synoviae.*

As described, the liquid composition according to the invention can be produced using common techniques and materials. Details and examples of such a method, a use, or a process for preparing a liquid composition according to the invention, are described herein, and such procedures are readily applicable by a person skilled in the art, using routine materials and methods.

For example, the NADES for the invention can be produced at industrial scale and is then formulated into a liquid composition according to the invention by admixing with a preparation of live Mollicutes bacteria. The mixture is then filled-out into appropriately sized containers. The various stages of the manufacturing process can be monitored by adequate tests, for instance by biochemical- or immunological tests for the quality and quantity of the bacteria.

Therefore, in a further aspect the invention provides a method for the manufacture of the liquid composition according to the invention, the method comprising the steps of:

a. preparing the NADES, and b. admixing said NADES with live Mollicutes bacteria.

Conveniently the two steps of the method according to the invention can be performed separated in time and/or in place, with intervening storage, transport, or even further steps. This will allow flexibility of operation in planning and logistics.

The manufacture of the NADES for use in the method according to the invention can be done using routine tools and methods. One convenient way is to apply heating of the combined compounds to a temperature that allows them to mix and solubilise, e.g. as in autoclaving. However, some compounds or compositions of NADES for use in the invention may not tolerate too high temperatures; the skilled person can optimize and fine-tune such a process. The heating can e.g. be done in combination with stirring or sonification.

Also, one of the components to form the NADES can initially be dissolved in water in more or less concentrated form, after which it can be mixed with (a) further component(s). The NADES structure is then formed by removing the surplus of water. Preferably such removal is not done by freeze-drying. An alternative method is e.g. rotational evaporation in a waterbath at 70° C. for several hours under reduced atmospheric pressure.

The composition comprising the live Mollicutes bacteria for use in the method according to the invention can conveniently be derived in different ways, from a culture in vivo, but preferably from an in vitro culture of the bacterium in a suitable medium. Such bacterial cultures can be made at any desired size or volume, up to several 1000 litres in large scale industrial size fermenters applying automated controls and monitoring techniques.

The bacteria are then harvested from the culture in a way that depends on the characteristics of the bacterium: as the supernatant, the cell-pellet, or as a whole culture. Next the bacteria are admixed with the NADES, either directly, or indirectly via first mixing the bacteria with a liquid, e.g. a buffer or medium.

The bacterial composition for use in the method of the invention can be prepared using further process steps such as concentration, e.g. using passage over ultra-filtration membranes. The bacterial composition is then checked for viability and quantity. All this is well-known to a skilled person.

The admixing of the NADES and the bacterial composition in the method according to the invention, is preferably done using aseptic techniques.

The order and the way of admixing is not critical, in that the NADES may be added to the bacterial composition, or the other way around. Preferably any mechanical mixing used will be low speed and low impact, to prevent unnecessary shear forces on the bacteria. Further, the mixing and/or filling can be done in a protective atmosphere of an inert gas (e.g. nitrogen), to reduce oxygen exposure.

Convenient equipment for mixing and filling of relatively viscous liquids is available from a variety of suppliers of process-equipment.

In a further aspect, the invention provides the use of a NADES as described for the invention, as a stabiliser in a liquid composition comprising live Mollicutes bacteria.

The 'stabiliser', the liquid 'composition', the 'live Mollicutes bacteria' are all as defined in any one or more of the embodiments as described herein for the invention.

As described, an advantageous utilisation provided by the present invention is in the medical use of the liquid composition according to the invention, as a bacterial vaccine.

Therefore, in a further aspect the invention provides the liquid composition according to the invention, or as obtainable by the method for the manufacture according to the invention, for use as a vaccine against infection or disease caused by Mollicutes bacteria.

Similarly, in a further aspect the invention provides a liquid vaccine for use against infection or disease caused by Mollicutes bacteria, the vaccine comprising the liquid composition according to the invention, or as obtainable by the method according to the invention.

And, in a further aspect the invention provides the use of a NADES as described for the invention as a pharmaceutically acceptable carrier in a liquid vaccine according to the invention.

A "vaccine" is well known to be a composition that has a medical effect. A vaccine comprises an immunologically active component, and a pharmaceutically acceptable carrier. The 'immunologically active component', in the present case is represented by the live Mollicutes bacteria. The vaccine is recognised by the immune system of the target animal, which induces a protective immunological response. The response may originate from the targets' innate- and/or from the acquired immune system and may be of the cellular- and/or of the humoral type.

A vaccine generally is efficacious in reducing the severity of an infection, for example by reducing the number of the pathogens present or shortening the duration of the pathogen's replication in a host animal.

Also, or possibly as a result thereof, a vaccine generally is effective in reducing or ameliorating the (clinical) symptoms of disease that may be caused by such infection or replication, or by the target's response to that infection or replication.

The "pharmaceutically acceptable carrier" for the invention is a liquid of a high grade of purity and preferably sterile. In the present case the carrier is a NADES as defined herein. The carrier can comprise further additives, such as stabilisers, anti-oxidants, or preservatives.

Details on 'infection or disease caused by Mollicutes bacteria' are well known in the art, and are for example described in handbooks such as: the Merck veterinary manual (supra), and Diseases of Poultry, 12th edition, 2008, Wiley-Blackwell, ISBN: 0813807182.

The liquid vaccine according to the invention comprises an amount of live Mollicutes bacteria that is immunologically effective.

A skilled person in the field of the invention will be more than capable of determining and optimising such immunologically effective amount of live Mollicutes bacteria in a liquid vaccine according to the invention, e.g. by monitoring the immunological response following vaccination. Also, in the case of a non-human animal target, a challenge infection can be given, followed by monitoring the targets' signs of disease, clinical scores, and spread and dissemination of the pathogen, and comparing these results to a vaccination-challenge response seen in mock-vaccinated animals.

Ways to determine the amount of live bacteria in a vaccine dose or in an animal sample are well-known in the art, and will typically employ techniques of bacterial culturing and counting. Conveniently such an amount of bacteria can be expressed as a number value, e.g. in CFU.

The targets for the liquid vaccine according to the invention are humans or non-human animals in need of a vaccination against infection or disease caused by a pathogenic form of the particular live Mollicutes bacterium that is comprised in the vaccine. The age, weight, sex, immunological status, and other parameters of the target to be vaccinated are not critical, although it is favourable to vaccinate healthy, uninfected targets, and to vaccinate as early as possible to prevent any field infection.

A liquid vaccine according to the invention may additionally comprise other compounds, such as an additional antigen or micro-organism, a cytokine, or an immunostimulatory nucleic acid comprising an unmethylated CpG, an adjuvant, etc. Alternatively, the liquid vaccine according to the invention, may itself be added to a vaccine.

The liquid vaccine according to the invention can advantageously be combined with one or more further antigens or micro-organism, e.g. derived from a micro-organism pathogenic to an intended human or non-human animal target. Such a further antigen may itself be an infectious micro-organism, live, attenuated, or inactivated, or can be a subunit, extract or fraction, etc. The further antigen may consist of a biologic or synthetic molecule such as a protein, a carbohydrate, a lipopolysaccharide, a lipid, or a nucleic acid molecule.

The liquid vaccine according to the invention may comprise a preservative, such as thimerosal, merthiolate, phenolic compounds, and/or gentamicin. Preferably no preservative is employed.

The liquid vaccine according to the invention may comprise a stabiliser, although preferably such stabiliser is not a variable or undefined compound as described herein.

The liquid vaccine according to the invention may comprise an antioxidant, such as an ascorbic acid, citrate, methionine, or a tocopherol.

The liquid vaccine according to the invention can be used either as a prophylactic- or as a therapeutic treatment, or both.

The liquid vaccine according to the invention can serve as an effective priming vaccination, which can later be followed by one or more booster vaccination(s), with the same or with a different vaccine.

The liquid vaccine according to the invention can be prepared using well-known techniques, that will incorporate the methods for the manufacture of the liquid composition according to the invention.

Therefore, in a further aspect the invention provides for the use of a NADES as described for the invention, for the manufacture of a liquid vaccine according to the invention.

Such manufacture will incorporate microbiological tests for sterility, and absence of extraneous agents; and ultimately vaccination-studies in animals for confirming efficacy and safety. After completion of the testing for quality, quantity, sterility, safety and efficacy, the vaccine product can be released for sale.

All these are well known to a skilled person, and general techniques and considerations that apply to the manufacture of vaccines under well-known standards for pharmaceutical production are described for instance in governmental directives and regulations (Pharmacopoeia, 9CFR) and in well-known handbooks (Pastoret, Lippincot, both supra).

The liquid vaccine according to the invention can be administered to a human or non-human animal in the form in which it is supplied for example by a pharmaceutical manufacturer. However, depending on the specific composition of a particular embodiment of the liquid vaccine according to the invention, it may be favourable to make a dilution of the liquid vaccine. This may facilitate the actual administration to a target for example by reducing the viscosity, or may reduce local reactions upon vaccination of the target.

The diluent for such dilution will typically be a liquid and may be provided separate from the liquid vaccine composition according to the invention. Preferably, the diluent is provided together with the liquid vaccine according to the invention, e.g. as a kit of parts.

Therefore, in a further aspect, the invention relates to a kit of parts, comprising at least two containers: one container comprising the liquid vaccine according to the invention, and one container comprising a liquid diluent.

A "liquid diluent" for diluting the liquid vaccine according to the invention, e.g. for inclusion in the kit of parts according to the invention, is a liquid that is suitable for diluting the liquid vaccine according to the invention. The liquid diluent can therefore be aqueous, such as water or a buffer. However, because of the low water content of the liquid vaccine according to the invention, the diluent can also be oily, or can be an emulsion of oil and water, e.g. an oil-in-water, a water-in-oil, or a double emulsion.

In one embodiment the liquid diluent may itself be a liquid vaccine, for example a reconstituted freeze-dried live vaccine, or an emulsion-vaccine.

The choice of liquid diluent for diluting the liquid vaccine according to the invention, e.g. for inclusion in the kit of parts according to the invention, will depend on several factors, such as: the intended use of the vaccine after it is diluted; the Mollicutes bacteria that it comprises; the intended human- or non-human animal target for the vaccination, etcetera. A skilled person is perfectly capable of selecting, preparing, and applying such a diluent.

In an embodiment of the kit of parts according to the invention, the kit comprises instructions for use of the kit and/or of its component parts. In preferred embodiments the instructions for use are provided on or with one or more of the component parts of the kit; or are provided by way of a reference to instructions in electronic form, such as information viewable on, or downloadable from, an internet website, e.g. from the manufacturer or the distributor of the kit.

In an embodiment the kit of parts is a box comprising the at least two containers, and comprising instructions for use which are displayed on an information carrier (e.g. a card, or a leaflet) comprised on, with, or within the box.

In an embodiment of the kit of parts, the kit may also be an offer of the component parts (relating to commercial sale), for example on an internet website, for use in a method of vaccination according to the invention.

The liquid vaccine according to the invention, or the liquid vaccine that can be manufactured by a method or a use according to the invention, or the liquid vaccine in diluted form as can be prepared e.g. using the kit of parts according to the invention, is intended for administration to a human- or non-human animal target in need of such vaccination. The vaccination induces active immunisation in order to reduce infection and/or of signs of disease that may be caused by an infection with a non-attenuated counterpart of the live Mollicutes bacteria for the invention. In turn this leads in the target human- or non-human animal to a reduction of the number, the intensity, or the severity of lesions and consequential clinical signs of disease caused by the bacterial infection. Such a vaccine is colloquially referred to as a: vaccine 'against' the particular Mollicutes bacterium, or as a 'Mollicutes vaccine'.

Therefore, in a further aspect, the invention provides the liquid vaccine according to the invention for use in a method for the protection of a human- or non-human animal target against infection and/or disease caused by a pathogenic form of the live Mollicutes bacteria comprised in said liquid vaccine.

Such a "pathogenic form of the live Mollicutes bacteria comprised in said liquid vaccine", is for example the unattenuated parent Mollicutes bacterium from which an attenuated form of the Mollicutes bacterium for the invention was generated. Alternatively, such pathogenic form bacteria can be readily derived from a variety of sources, as described herein. A person skilled in the art of the invention is perfectly able to determine whether a Mollicutes bacterium is a pathogenic form, for example by comparative testing in vitro or in vivo as described herein.

The "method for the protection" involves the administration of the liquid vaccine according to the invention to said human- or non-human animal target, so that the vaccine can 'take' (i.e. establish a protective infection) and display its favourable immunologic effects in the target.

In a further aspect the invention provides a method for the vaccination of a human- or non-human animal target against infection or disease caused by Mollicutes bacteria, the method comprising the administration to said target of the liquid vaccine according to the invention or comprising the use of the kit of parts according to the invention.

In the method for the vaccination according to the invention, the liquid vaccine according to the invention can be employed for direct administration to a human- or non-human animal target. Alternatively, the liquid vaccine according to the invention can be administered to a human- or non-human animal target in a diluted form. This latter embodiment of a method of vaccination according to the invention, may facilitate the handling and administration by injection because of the reduced viscosity. Alternatively, or additionally, the administration in diluted form may reduce local reactions in the human- or non-human animal target, for example resulting from tissue irritation at the site of inoculation.

Vaccination according to the method of the invention can be performed by parenteral route, i.e. through the skin, e.g.: intramuscular, intraperitoneal, intradermal, submucosal, or subcutaneous. Preferred route of parenteral administration of the liquid vaccine composition according to the invention is by intramuscular or by subcutaneous injection.

Further the liquid vaccine according to the invention can be administered by enteral or mucosal route, i.e. via eye drop, nose drop, orally, enteric, oro-nasal drop, spray, aerosol, etcetera.

Alternatively, the liquid vaccine according to the invention can be administered to a target via a method of mass administration, such as via drinking water, coarse spray, atomisation, on-feed, etcetera. A further alternative is the administration to embryonal birds, by in ovo route.

It goes without saying that the optimal route of administration of a liquid vaccine according to the invention will depend on the specifics of the vaccine that is used, and on the particular characteristics of the target. A skilled person is perfectly capable of selecting and optimising such route and method of administration.

The liquid vaccine according to the invention, can be administered by parenteral route in a volume that is acceptable for the target human- or non-human animal, and can for instance be at a volume of between about 0.01 ml and about 10 ml. Preferably one dose is a volume between about 0.05 ml and about 5 ml, more preferably one dose is between 0.1 ml and 3 ml.

When administered by intramuscular route, the volume of one dose is preferably between about 0.5 ml and about 3 ml, more preferably between about 1 ml and about 2 ml.

When administered by intradermal route, the volume of one dose is preferably between about 0.1 ml and about 0.5 ml, more preferably about 0.2 ml.

When administered in ovo, the volume of one dose is preferably between about 0.01 ml and about 0.5 ml, more preferably about 0.05 ml.

The method, timing, and volume of the administration of a liquid vaccine according to the invention is preferably integrated into existing vaccination schedules of other vaccines that the target human- or non human animal may require, in order to reduce stress to the target and to reduce labour costs. These other vaccines can be administered in a simultaneous, concurrent, or sequential fashion, and in a manner compatible with their registered use.

It is well within reach of the skilled person to further optimise a liquid vaccine according to the invention. Generally, this involves the fine-tuning of the efficacy of the vaccine to further improve its provided immune-protection. This can be done e.g. by adapting the dose, volume, or antigen content of the vaccine, or by application via a different route, method, or regime. All these are within the scope of the invention.

The invention will now be further described by the following, non-limiting, examples.

EXAMPLES

Example 1: Methods and Materials 1.1 Preparing the NADES Formulations

NADES can be prepared by mixing of the desired components, which can be accelerated by heating and/or addition of a small amount of water. The samples of NADES as further tested and described herein below were prepared by dissolving the relevant compounds in water via sonification in a waterbath. The required quantities of compounds were added to a flask. The flask was briefly shaken or vortexed, to mix the powders. Next the required amount of water was added. This mixture was placed in a sonication-waterbath, set at 45° C., with sonication up to several hours, until a NADES was formed. During sonication temperatures of up to 80° C. could be reached.

1.2 Measurements of Water Activity

Samples

For biological containment purposes the water activities were measured of samples of NADES preparations, so without live bacteria. However, when knowing the amount of aqueous bacterial composition that will be added to the NADES to form the liquid vaccine composition according to the invention, the resulting water activity of the combination of NADES and bacterial composition can be calculated according to Dai et al. (2015, Food Chem., vol. 187, p. 14-19).

Sample Preparation

An amount of NADES sample was transferred to a 10 ml glass vial in order to reach a fill height of approx. ¼ of the vial. For each sample coded vials were filled in duplicate. The vials were closed using an aluminium crimp cap with PTFE stopper, and were placed at room temperature for 12 hours to reach an equilibrium between sample and headspace.

Equipment

The moisture vapour pressure in the headspace of the samples was determined using the Lighthouse® FMS-1400 Moisture/Pressure analyser. The samples were inserted into the sample chamber as such. Before sample measurement the system was calibrated using calibration headspace pressure standards in the range of 0-0.2 $a_w$. Also, saturated salt standards were used to calibrate and recalculate the non linear range from 0.2-1 $a_w$.

Calibration

To calibrate the machine over the full range from $a_w$ 0-1, and to create a reference line of water activity values, a number of standard samples were measured: next to pure water 5 samples of specific saturated salt-solutions were used, and for each of the 6 standards duplo samples were measured in 3 fold. By setting the measured value for pure water to 1.000, the other standard values were determined at $a_w$ of: 0.8511, 0.7547, 0.5438, 0.3307, and 0.1131. Also, a series of certified vapour pressure standards were measured.

Results of $a_w$ measurements are included in Table 1.

1.3 Testing the DSC Profile of a NADES

Differential scanning calorimetry (DSC) analysis was done on a Q2000 DSC apparatus from TA Instruments using Thermal Analysis software. For a full DSC profile, samples were first equilibrated at 40° C. and cooled to −90° C. at 5° C./min, followed by equilibration for 5 min at −90° C. after which samples were heated again to 40° C. at 5° C./min. This cycle of cooling and heating was repeated a second time on the same sample to investigate phase hysteresis. The Tg of a sample was determined by the software from the heating curve by the midpoint of the stepwise shift in the baseline, indicating a change in thermal conductivity due to increased mobility during the glass transition.

A representative DSC profile of a NADES for the invention is presented in FIG. 1, for a NADES formed at a molar ratio for proline, sorbitol, and water of 1:1:2.5.

FIG. 1 shows the steep shift of the base line, here between −41 and −45° C., that indicates a glass-transition, which corresponds with the properties of an effective NADES for the invention. This profile is essentially different from the one as presented by Qiao et al. (supra), in their FIG. 4, of a NADES that was overly diluted and became an aqueous composition; that shows an essentially even baseline, with raise and drop of the heat flow upon the forming and melting of water-ice crystals; so-called 'cold-crystallisation'.

1.4 Mixing NADES and Bacterial Compositions

NADES preparations were blended 9+1 v/v with bacterial compositions in a laminar flow cabinet. Samples were either gently mixed using a roller bank; vortexed; or stirred briefly using a sterile inoculation loop, depending on sample size. From these samples 1 ml aliquots were filled into 3 ml glass vials that were capped with rubber stopper and metal cap.

1.5 Stability Assays

For each test sample a unique vial was stored at refrigerated conditions (2-8° C.), frozen conditions (−20° C.) or at room temperature (20° C.). After a defined period, the vial was opened and a serial tenfold dilution in PBS was prepared from 10^−1 to 10^−10 dilution. For at least three dilutions a 50 μl sample was plated on agar plates supporting the growth of the specific bacterium, in duplo. Next, plates were incubated at 37° C. and 5% $CO_2$ for 5-8 days until colonies were of sufficient size to be counted. From this the titre of the Mollicutes was calculated, whereby between 30 and 300 colonies were counted. The titre was expressed as colony forming units per ml sample (CFU/ml). From the data points of the different vials that are tested at the different time points, a graph of the stability data was created, as is represented in FIGS. 2 and 3.

Example 2: Composition of NADES for Use in the Invention

A large number of different NADES compositions were prepared for use in the invention, with different compounds, with different molar ratios, and with different water contents.

Table 1 below lists a number of the most effective NADES formulations; these yielded clear liquid solutions, that were fluid at room temperature (about 20° C.). Details on their composition and water content are provided. For several of the samples prepared, the water activity was determined, and the results are included.

TABLE 1

Compositions and properties of a representative number of NADES for the invention

| | | | | Molar ratios | % water (w/w) | $a_w$ (21° C.) | Tg (° C.) |
|---|---|---|---|---|---|---|---|
| Proline | Sorbitol | — | WFI | 1:1:2.5 | 13.1 | 0.39 | −42 |
| Betaine | Sorbitol | — | WFI | 1:1:2.5 | 13.1 | 0.32 | −50 |
| Arginine | Sorbitol | — | WFI | 1:2:6 | 15.9 | 0.60 | −48 |
| Choline-Cl | Xylitol | — | WFI | 2:1:2.5 | 9.5 | 0.18 | −75 |
| Xylitol | Sorbitol | Trehalose | WFI | 2:2:1:10 | 14.7 | 0.59 | −49 |

Example 3: Results of Bacterial Stability Assays

For *M. synoviae* and *M. gallisepticum* bacteria, comprised in liquid compositions according to the invention, stability assays were performed over an extended period of time, and temperatures of 2-8° C. and at room temperature (about 20° C.).

The incubation at room temperature for 8 weeks can serve as an expedited stability test, indicative of the effect of incubation for 1-2 years at 4° C. This is thus a very severe attack on the bacteria's viability, and not all samples were expected to survive under those conditions.

Conclusions from the Stability Results

The inherent poor stability of both *M. synoviae* and *M. gallisepticum* bacteria during storage was demonstrated by the control, being the 1+9 v/v admixture in standard Phosphate Buffered Saline (PBS). Please refer to FIGS. 2 and 3 for exemplary details. In this control liquid composition, already at the first timepoint tested no bacterial colonies could be detected anymore, at any of the investigated dilutions. This applied both to storage conditions at 2-8° C. and at RT.

From these control samples, it was concluded that there was no detectable survival of either *M. synoviae* or *M. gallisepticum* in PBS.

Surprisingly, and in sharp contrast with the PBS controls, both *M. synoviae* and *M. gallisepticum* showed impressive survival when combined with NADES in a liquid composition according to the invention. When admixed 1+9 v/v with different NADES, measurable titres were obtained upon storage at 20° C. for up to 8 weeks.

For *M. synoviae* the stabilizing effect at 20° C. was strongest with the NADES' Betaine:Sorbitol:WFI at 1:1:2.5 molar ratio, and Sorbitol:Xylitol:Trehalose:WFI at 2:2:1:10 molar ratio. Upon storage at 2-8° C. for up to 6 months impressive survival titres were found, with losses of less than 3 Log 10 CFU/ml for several NADES.

For *M. gallisepticum* the stabilizing effect at 20° C. was strongest with the NADES' Arginine:Sorbitol:WFI at 1:2:6 molar ratio, and Proline:Sorbitol:WFI at 1:1:2.5 molar ratio. Upon storage at 2-8° C. for up to 3 months, impressive survival titres were found, with losses of less than 3 Log 10 CFU/ml for several NADES.

Example 4: Administration of NADES to Experimental Animals

To assess the ease of administration, and the safety of a NADES for use in the invention in target animals, examples of a NADES were administered to experimental animals and to post mortem materials.

For this purpose, two variants of a Proline:Sorbitol based NADES, were made and tested: one with high (NADES 3A) and one with low (NADES 3B) viscosity. These served to compare the administration-properties of NADES for the invention at two extremes of the viscosity spectrum. The characteristics of NADES 3A are described in Table 1. Further, their viscosities were measured using standard conditions: at about 20° C., using a Brookfield® DV-I+ viscometer, utilising spindle type No. 62, for 30 seconds at 60 r.p.m., in a standard measuring cup of about 80 ml volume.

Handling

The high viscosity NADES 3A, could be pushed through a hypodermic needle of size 21 G or less, i.e. a needle with an outer diameter of 0.8 mm or more.

TABLE 3

NADES formulations tested by administration to animals

| # | Ionic species | Polyol | molar ratio Pro:Sor:WFI | | | Viscosity (mPa · s) |
|---|---|---|---|---|---|---|
| 3A | Proline | Sorbitol | 1.0 | 1.0 | 2.5 | 5197 |
| 3B | Proline | Sorbitol | 1.0 | 1.0 | 10.0 | 33.4 |
| 3C | Proline | Sorbitol | 1.0 | 1.0 | 5.0 | 289 |

Subcutaneous Administration In Vivo

The NADES formulations 3B and 3C were administered by subcutaneous injection, in a safety study in dogs. Special attention was given to any adverse reactions that could occur after the administration of the stabilizer formulations, either locally or systemically.

Both formulations were prepared as described before, by heating and sonification of proline, sorbitol, and water for injection, in a closed vial, resulting in a clear and homogeneous liquid. Additionally, they were filter-sterilised, and their bioburden and endotoxin levels were determined. Both formulations were found to score below the lowest dilution standard of 1 unit/ml, meeting the general acceptance criteria for sterile formulations. The NADES 3C formulation was prepared by diluting 1 volume part NADES 3A with 9 volume parts WFI, resulting in a formulation with Proline:Sorbitol:WFI in 1:1:5 ratio, and a viscosity of 289 mPa·s. NADES 3B has a viscosity of 33.4 mPa·s.

Six healthy beagle dogs of 7 months old, were divided into two groups of 3 dogs. Each group was assigned to a NADES formulation, and received two doses of 1 ml of the assigned formulation, using a 1 ml syringe and a 21 G ⅝ needle by subcutaneous inoculation, with a two-week interval. Group 1 dogs were given the low viscosity NADES 3B, and the Group 2 dogs received the high viscosity NADES 3C. All dogs were clinically monitored daily throughout the study, including for local reactions at the site of the inoculations.

The vaccinations were performed in the scruff of the neck; the first vaccination was done on the left side, and the second vaccination was done on the right side of the neck. The vaccination sites were shaved prior to each administration, and the injection site was circled with a marker pen. No discomfort was observed during any of the injections. At 4 hours post-injection, injection sites were palpated, and little or no material was palpable at the injection sites, and no swelling or redness was observed.

Rectal temperatures were taken on days −3, −2, −1 before each of the vaccinations; at the day of vaccination: just before vaccination and 4 hours after vaccination; and next daily for seven days post vaccination.

Throughout the whole study no significant increase in body temperature was observed in any of the dogs and no clinical adverse effects were observed.

In conclusion: the inoculation of NADES formulations 3C or 3B by subcutaneous route to dogs, did not induce any adverse inoculation reaction, neither locally, nor systemically.

Intra-Nasal Administration

Two NADES formulations: 3A and 3B were tested for their pattern of spread on the mucosal surface of the nose, when administered intranasally. Both NADES formulations were tested as such, without adding water. Consequently, NADES 3A has a viscosity of 5197 mPa·s, and NADES 3B of 33.4 mPa·s. A spatula tip of 'patent blue' colourant was added to 30 ml of each of the NADES formulations, to obtain a deep blue colour. As a control PBS with colourant was used.

Calf heads were obtained post-mortem from calves of about 2-4 weeks old. The administration was done holding the head in an upright position mimicking the position of a calf during i.n. vaccination in the field, with the nostrils tilted slightly upwards.

The liquids were then administered according to a standard procedure for intranasal vaccination, whereby a 2.5 ml syringe without needle, containing 1.5 ml liquid, was placed into a nostril, and then the liquid was squirted out in one steady flow. Next the head was dissected into two halves and the septum was removed and inspected for presence of blue colour in the intranasal tract.

For all samples it was observed that the blue liquids had moved easily through the nasal tract. The low viscosity of the PBS sample allowed for easy injection, but all liquid rushed through quickly. A blue colour was observed all through the whole of the nasal cavity including the beginning of the trachea.

The injection of NADES 3A with the very high viscosity took a little force to inject out of the syringe. Also, as expected, it took longer for the blue liquid to emerge below the head. After dissection of the head, it was observed that also this viscous liquid had spread evenly through the intranasal tract, where it appeared to have formed a thick layer, leaving more material in the nasal tract. This indicates an improved retention and less progression to the upper respiratory tract would occur, when administered to a life calf during i.n. vaccination.

The effect of the administration of the NADES 3B formulation, with the low viscosity, closely resembled that of the PBS sample, where the liquid rushed through the nasal cavity.

In conclusion: it was possible to monitor the distribution of coloured preparations with different viscosity after intranasal injection into calve-heads. Distribution of the liquid as judged by the blue colour was comparable for the two NADES preparations and PBS, with some difference with regard to ease of administration and amount of residual material, whereby the NADES 3A formulation was a little more difficult to eject, but resulted in a thicker layer of residue within the nasal tract. This suggests a delayed release of antigen from such viscous NADES formulations may be obtained.

Example 5: Comparative Measurements on an Aqueous Stabiliser

An aqueous stabiliser composition as described in WO 2015/121463 was prepared having: 30% w/w Sorbitol+0.6 M Arginine in 0.04 M PBS. This composition was tested for its properties such as water activity and DSC profile, to clarify that it does not possess the characterising features which make a composition a NADES as defined and outlined hereinabove.

Water Activity

Determination of $a_w$ was done by way of headspace vapour pressure measurement, as described in WO 2019/122329, Example 1. Result for water activity was determined in duplo, giving an average $a_w$ of 0.89. Clearly, this high level of available water demonstrates that this composition is not a NADES.

DSC Profile

Determination of the DSC profile of the aqueous prior art stabiliser was done as described herein in Example 1.3.

Figure 4:
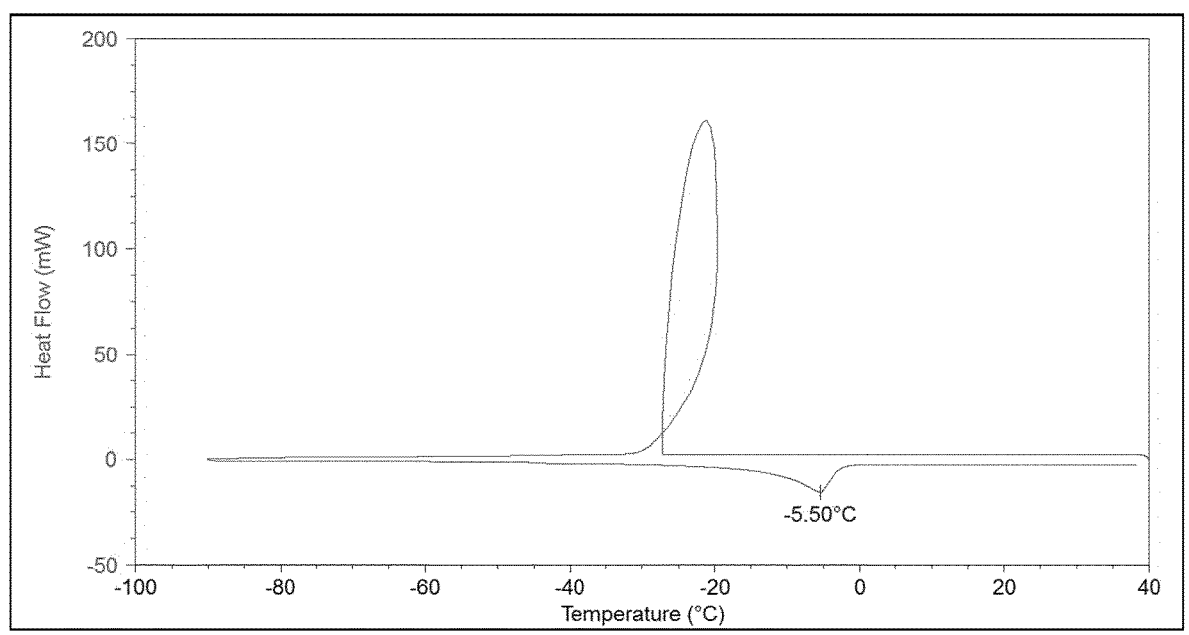

The results are presented in FIG. 4, whereby (as in FIG. 1 herein) the upper horizontal part of the graph presents the cooling phase from 40° C. to −90° C. at 5° C./min (going right to left), and the bottom horizontal part the heating phase from −90° C. to 40° C. at 5° C./min (left to right).

During the cooling, an extensive and sudden crystallisation of free water into ice is observable, at a temperature of about −27° C. Next, upon re-heating a typical ice-crystal melting profile was observed with a peak at −5.5° C.

Further, in FIG. 4, during the heating phase, the horizontal base line after the ice-melt returns to the same level at which it was before the melt. This signifies there was no change in the thermal capacity of that sample, which is clearly different from the stepwise baseline shift that is typically observed in the case of a glass transition.

Also it is significant that the ice-melt in FIG. 4 occurs at a much higher temperature (−5° C.) than the glass-transition in FIG. 1 (−45° C.), again illustrating that the sample tested in FIG. 4 was not a deep-eutectic mixture.

In FIG. 4, both peaks, the high melting temperature, and the return of the base line to its previous level, are all indicative for the formation and the melting of ice-crystals, and therefore demonstrate that the composition tested had much free water present, and thus was not a NADES.

On the contrary however, in the sample of FIG. 1 (a NADES according to the invention), no ice crystals were formed or melted, and a clear glass-transition shift of the base line was found.

Example 6: Additional Stability Results: *M. bovis*

A further species of Mollicutes bacteria was tested for stabilisation in the liquid compositions according to the invention: *Mycoplasma bovis*. Experiments were performed essentially as described herein in Examples 1-3 for *M. synoviae* and *M. gallisepticum*.

Results of stability assays in different compositions according to the invention, and either at room-temperature or at 2-8° C. are presented in FIG. 5:
  panel A: room temperature, up to 10 weeks; and
  panel B: 2-8° C., up to 26 weeks of incubation.

Starting titre was 9.9 Log 10 CFU/ml. In PBS (the negative control) some survival was observed at two weeks of incubation, both at room temperature and when refrigerated. However no viable cells could be retrieved anymore in samples incubated for longer periods in PBS.

At room temperature good initial stability (2-4 weeks of incubation) was obtained in several of the NADES compositions. However best results were found when using Arginine:Sorbitol:water (2:1:6), which was able to stabilise this bacterium for at least 10 weeks at room temperature.

At refrigerated incubation, a similar picture was observed: good initial stabilisation for 6-13 weeks, was observed for several of the compositions tested. Best long-term stabiliser (26 weeks of incubation) was also Arginine:Sorbitol:water (2:1:6), although the differences observed between the different compositions tested were not as big as for room temperature incubation.

Overall, *M. bovis* could effectively be stabilised without freeze-drying in the liquid compostions according to the invention, at different storage temperatures above freezing.

Example 7: Extended Stability Test Results

Stability test results for *M. synoviae* and *M. gallisepticum* in liquid compositions according to the invention, were obtained from a continued incubation up to 1 year at 2-8° C.

These data result from the same series of samples as described in Example 3, and extend on the results as depicted in FIGS. 2B and 3B herein.

The extended results are provided in FIG. 6:
  panel A: *M. synoviae* at 2-8° C. up to 54 weeks; and
  panel B: *M. gallisepticum* at 2-8° C. up to 52 weeks of incubation.

For *M. synoviae*, three of the tested liquid compositions according to the invention can stabilise the viability of these bacteria for at least a year at 2-8° C.; whereby Proline:Sorbitol:water (1:1:2.5) and Betaine:Sorbitol:water (1:1:2.5) showed the same final results.

For *M. gallisepticum*, viable bacteria were only retained until 52 weeks of incubation at 2-8° C., in Betaine:Sorbitol:water (1:1:2.5).

LEGEND TO THE FIGURES

FIG. 1:
Differential scanning calorimetry profile of a NADES formed at a molar ratio for proline, sorbitol, and water of 1:1:2.5.
FIG. 2:
Stability results of *Mycoplasma synoviae* in liquid compositions with different NADES.
Panel A: incubated at room temperature; Panel B: incubated at 2-8° C.
FIG. 3:
Stability results of *Mycoplasma gallisepticum* in liquid compositions with different NADES.
Panel A: incubated at room temperature; Panel B: incubated at 2-8° C.
FIG. 4:
DSC profile of an aqueous stabiliser from the prior art, comprising 30% w/w sorbitol and 0.6 M arginine in 0.04 M PBS.
FIG. 5
Stability data for *M. bovis* in NADES, at room temperature (A), and at 2-8° C. (B).
FIG. 6:
Long term stability data of *M. synoviae* (A) and of *M. gallisepticum* (B) in NADES at 2-8° C.

The invention claimed is:

1. A liquid composition for protection against infection or disease caused by Mollicutes bacteria, comprising live Mollicutes bacteria and a stabiliser, wherein the stabiliser is a natural deep-eutectic solvent (NADES), wherein the composition has a water activity of 0.85 or less, and a water content of 50% w/w or less.

2. The liquid composition of claim 1, wherein the NADES comprises an organic salt and a polyol.

3. The liquid composition of claim 1, wherein the NADES comprises two or more compounds that are all polyols.

4. The liquid composition of claim 2, wherein the polyol is a sugar or a sugar-alcohol.

5. The liquid composition of claim 4, wherein the sugar is selected from sucrose and trehalose, or in that the sugar-alcohol is one or more selected from: erythritol, xylitol, and sorbitol.

6. The liquid composition of claim 2, wherein the organic salt is one or more selected from salts of: betaine, proline, choline, methionine, and arginine.

7. The liquid composition of claim 1, wherein the Mollicutes bacteria are attenuated in respect of their pathogenic properties.

8. A method for manufacturing the liquid composition of claim 1, comprising the steps of;
   a. providing the NADES, and
   b. admixing the NADES with live Mollicutes bacteria, wherein the admixture has a water activity of 0.85 or less, and a water content of 50% w/w or less.

9. A liquid composition obtainable by the method of claim 8.

10. A kit of parts comprising at least two containers: one container comprising the liquid composition of claim 1, and one container comprising a liquid diluent.

11. A method of vaccinating a human or non-human animal target against infection or disease caused by Mollicutes bacteria, comprising administering to said target the liquid composition of claim 1.

12. A method of vaccinating a human or non-human animal target against infection or disease caused by Mollicutes bacteria, comprising mixing from the kit of parts of claim 10, the contents of the container comprising the liquid composition with the contents of the container comprising a liquid diluent to form a mixture and then administering the mixture to the human or non-human animal target.

13. A vaccine for protection against infection or disease caused by Mollicutes bacteria, comprising the liquid composition of claim 9.

14. A method of vaccinating a human or non-human animal target against infection or disease caused by Mollicutes bacteria, comprising administering to the target the liquid vaccine of claim 13.

* * * * *

UNITED STATES PATENT AND TRADEMARK OFFICE
CERTIFICATE OF CORRECTION

| | | |
|---|---|---|
| PATENT NO. | : 12,214,027 B2 | Page 1 of 1 |
| APPLICATION NO. | : 17/441768 | |
| DATED | : February 4, 2025 | |
| INVENTOR(S) | : Martin Piest et al. | |

It is certified that error appears in the above-identified patent and that said Letters Patent is hereby corrected as shown below:

In the Claims

Claim 5:
In Column 26, Line 59, replace "in that" with "wherein"

Claim 11:
In Column 27, Line 14, add "human or non-human animal" before "target"

Claim 12:
In Column 27, Line 20, replace "a" with "the"

Claim 14:
In Column 27, Line 28, add "human or non-human animal" before "target"
In Column 27, Line 29, delete "liquid" before "vaccine"

Signed and Sealed this
Eighteenth Day of March, 2025

Coke Morgan Stewart
*Acting Director of the United States Patent and Trademark Office*